(12) United States Patent
Snyder et al.

(10) Patent No.: US 8,071,378 B2
(45) Date of Patent: Dec. 6, 2011

(54) ZNF206: REGULATOR OF EMBRYONIC STEM CELL SELF-RENEWAL AND PLURIPOTENCY

(75) Inventors: Evan Yale Snyder, La Jolla, CA (US); Rodolfo Gonzalez, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 170 days.

(21) Appl. No.: 12/221,824

(22) Filed: Aug. 6, 2008

(65) Prior Publication Data

US 2009/0092616 A1    Apr. 9, 2009

Related U.S. Application Data

(60) Provisional application No. 60/963,850, filed on Aug. 6, 2007.

(51) Int. Cl.
 C12N 5/00 (2006.01)
 C12N 5/02 (2006.01)
 C12N 15/00 (2006.01)
(52) U.S. Cl. .................. 435/377; 435/455; 435/325
(58) Field of Classification Search .................. 435/377, 435/455, 325
 See application file for complete search history.

(56) References Cited

FOREIGN PATENT DOCUMENTS

WO    2007019398 A1    2/2007

OTHER PUBLICATIONS

Jaenisch and Young. Cell 132:567-582, 2008.*
Stem Cells: Scientific Progress and Future Research Directions. Dept. of Health and Human Services. Jun. 2001. </info/scireport/2001report>. Chapter 1: The Stem Cell, pp. 1-4.*
Zhang et al.: Nucleic Acids Research, vol. 34, No. 17, Oct. 2006, pp. 4780-4790.
Database UniProt [Online] Dec. 1, 2001, "RecName: Full=Zinc finger and SCAN domain-containing protein 10; AllName: Full=Zinc finger protein 206," XP002589475 retrieved from EBI accession No. UNIPROT:Q96SZ4Database accession No. Q96SZ4.
Database UniProt [Online] May 2, 2006, "SubName: Full=ZSCAN10 protein; Flags: Fragment;" XP002589476 retrieved from EBI accession No. UNIPROT:Q1WWM2 Database accession No. Q1WWM2.
Database EMBL [Online] Feb. 3, 2004, "Sequence 759 from Patent W002068579." XP002589477 retrieved from EBI accession No. EMBL:CQ714825 Database accession No. CQ714825.
Database EMBL [Online] Mar. 25, 2004, "*Homo sapiens* zinc finger and SCAN domain containing 10, mRNA (eDNA clone IMAGE:4000761 0), partial cds." XP002589478 retrieved from EBI accession No. EMBL:BC114452 Database accession No. BC114452.
Database EMBL [Online] May 15, 2001, "*Homo sapiens* cDNA FLJ14549 fis, clone NT2RM2001670, weakly similar to Zinc Finger Protein 29." XP002589479 retrieved from ESI accession No. EMBL:AK027455 Database accession No. AK027455.
Yu et al.: Journal of Biological Chemistry, vol. 284, No. 45, Nov. 2009, pp. 31327-31335.
Brandenberger et al: Nature Biotechnology, vol. 22. No. 6. Jun. 2004m oages 707-716.
Wang et al.: Journal of Biological Chemistry, vol. 282, No. 17, Apr. 2007, pp. 12822-12830.

* cited by examiner

*Primary Examiner* — Marcia S Noble
(74) *Attorney, Agent, or Firm* — Sam K. Tahmassebi; TechLaw LLP

(57) ABSTRACT

We have identified ZNF206, a novel repressor of human embryonic stem cell (hESC) differentiation. Repressing extra-embryonic endoderm development preserves the pluripotent state of human embryonic stem cells, and, conversely downregulating expression of ZNF206 in hESCs causes them to upregulate the expression of genes associated with the extra-embryonic endodermal lineage, down-regulate genes associated with the pluripotent state, and may lead to the further emergence of genes associated with even more differentiated lineages and phenotypes.

8 Claims, 14 Drawing Sheets

*Splicing causes a frameshift that results in an early termination codon (TGA)

ZNF206 Isoform 1 [148 amino acids; predicted weight 16.74 kd]
MLGESVPAALEQEQLGEVKLEEEEAVSPEDPRRPESRLRPEVAHQLFRCFQYQEDMGPRASLS
RLRELCGHWLRPALHTKKQILELLVLEQFLSVLPPHLLGRLQGQPLRDGEEVVLLLEGIHREPSHA
GPLVRGWGSGLSSMRMMGT

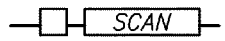

ZNF206 Isoform 2 [780 amino acids; predicted weight 86.78 kd]
MLGESVPAALEQEQLGEVKLEEEEAVSPEDPRRPESRLRPEVAHQLFRCFQYQEDMGPRASLS
RLRELCGHWLRPALHTKKQILELLVLEQFLSVLPPHLLGRLQGQPLRDGEEVVLLLEGIHREPSHA
GPLDFSCNAGKSCPRADVTLEEKGCASQVPSHSPKKELPAEEPSVLGPSDEPPRPQPRAAQPA
EPGQWRLPPSSKQPLSPGPQKTFQALQESSPQGPSPWPEESSRDQELAAVLECLTFEDVPENK
AWPAHPLGFGSRTPDKEEFKQEEPKGAAWPTPILAESQADSPGVPGEPCAQSLGRGAAASGP
GEDGSLLGSSEILEVKVAEGVPEPNPELQFICADCGVSFPQLSRLKAHQLRSHPAGRSFLCLCCG
KSFGRSSILKLHMRTHTDERPHACHLCGHRFRQSSHLSKHLLTHSSEPAFLCAECGRGFQRRAS
LVQHLLAHAQDQKPPCAPESKAEAPPLTDVLCSHCGQSFQRRSSLKRHLRIHARDKDRRSSEGS
GSRRRDSDRRPFVCSDCGKAFRRSEHLVAHRRVHTGERPFSCQACGRSFTQSSQLVSHQRVH
TGEKPYACPQCGKRFVRRASLARHLLTHGGPRPHHCTQCGKSFGQTQDLARHQRSHTGEKPC
RCSECGEGFSQSAHLARHQRIHTGEKPHACDTCGHRFRNSSNLARHRRSHTGERPYSCQTCG
RSFRRNAHLRRHLATHAEPGQEQAEPPQECVECGKSFSRSCNLLRHLLVHTGARPYSCTQCGR
SFSRNSHLLRHLRTHARETLY

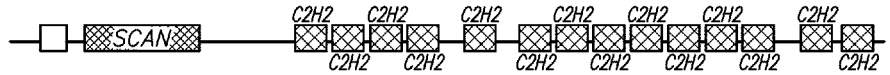

ZNF206 Isoform 3 [724 amino acids; predicted weight 80.39 kd]
MLGESVPAALEQEQLGEVKLEEEEAVSPEDPRRPESRLRPEVAHQLFRCFQYQEDMGPRASLS
RLRELCGHWLRPALHTKKQILELLVLEQFLSVLPPHLLGRLQGQPLRDGEEVVLLLEGIHREPSHA
GPLDFSCNAGKSCPRADVTLEEKGCASQVPSHSPKKELPAEEPSVLGPSDEPPRPQPRAAQPA
EPGQWRLPPSSKQPLSPGPQKTFQALQESSPQGPSPWPEESSRDQELAAVLECLTFEDVPENK
AWPAHPLGFGSRTPDKEEFKQEEPKGAAWPTPILAESQADSPGVPGEPCAQSLGRGAAASGP
GEDGSLLGSSEILEVKVAEGVPEPNPELQFICADCGVSFPQLSRLKAHQLRSHPAGRSFLCLCCG
KSFGRSSILKLHMRTHTDERPHACHLCGHRFRQSSHLSKHLLTHSSEPAFLCAECGRGFQRRAS
LVQHLLAHAQDQKPPCAPESKAEAPPLTDVLCSHCGQSFQRRSSLKRHLRIHARDKDRRSSEGS
GSRRRDSDRRPFVCSDCGKAFRRSEHLVAHRRVHTGERPFSCQACGRSFTQSSQLVSHQRVH
TGEKPYACPQCGKRFVRRASLARHLLTHGGPRPHHCTQCGKSFGQTQDLARHQRSHTGERPY
SCQTCGRSFRRNAHLRRHLATHAEPGQEQAEPPQECVGCGKSFSRSCNLLRHLLVHTGARPYS
CTQCGRSFSRNSHLLRHLRTHARETLY

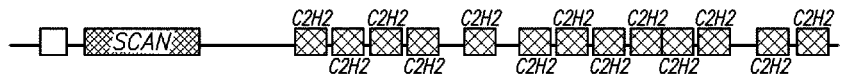

ZNF206 Isoform 4 [156 amino acids; predicted weight 17.93 kd]
MLGESVPAALEQEQLGEVKLEEEEAVSPEDPRRPESRLRPEVAHQLFRCFQYQEDMGPRASLS
RLRELCGHWLRPALHTKKQILELLVLEQFLSVLPPHLLGRLQGQPLRDGEEVVLLLEGIHREPSHA
GPLVPRAPHHGQRRVPEIRSWRLCWSA

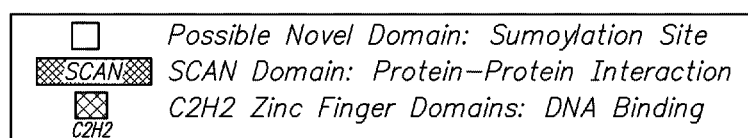

*FIG. 4C*

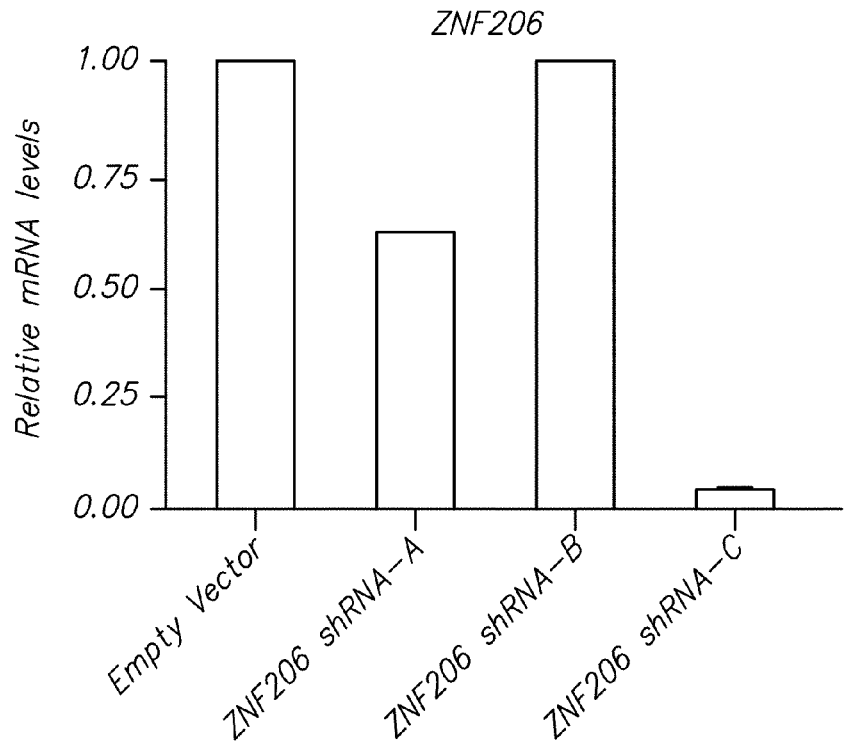

FIG. 6B

*Human ZNF206 Protein Sequence*
*Rabbit Polyclonal Antibody Target Sequence*

MLGBSVPAALEQEQLGEVKLEEEEAVSPEDPRRPESRLRPFVAHQLFRCFQYQEDMGPRASLSRL
RELCGHWLRPALHTKKQILELLVLEQFLSVLPPHLLGRLQGQPLRGEEVVLLLEGIHREPSHAGPL
DFSCNAGKSCPRADVTLEEKGCASQVPSHSPKKELPAEEPSVLGPSDEPPRPQPRAAQPAEPGQ
WRLPPSSKQPLSPGPQKTFQALQESSPQGPSPWPEESSRDQELAAVLECLTFEDVPENKAWPAH
PLGFGSRTPDKEEFKQEEPKGAAWPTPILAESQADSPGVPGEPCAQSLGRGAAASGPGEDGSLL
GSSEILEVKVAEGVPEPNPELQFKCADCGVSFPQLSRLKAHQLRSHPAGRSFLCLCCGKSFGRSSIL
KLHMRTHTDERPHACHLCGHRFRQSSHLSKHLLTHSSEPAFLCAECGRGFQRRASLVQHLLAHAQ
DQKPPCAPESKAEAPPLTDVLCSHCGQSFQRRSSLKRHLRIHARDKDRRSSEGSGSRRRSDRR
PFVCSDCGKAFRRSEHLVAHRRVHTGERPFSCQACGRSFTQSSQLVSHQRVHTGEKPYACPQCG
KRFVRRASLARHLLTHGGPRPHHCTQCGKSFGQTQDLARHQTSHTGEKPCRCSECGEGFSQSA
HLARHQRIHTGEKPHACDTCGHRFRNSSNLARHRRSHTGERPYSCQTCGRSFRRNAHLRRHLAT
<u>HAEPQQEQAEPPQEC</u>VECGKSFSRSCNLLRHLLVHTGARPYSCTQCGRSFSRNSHLLRHLRTHA
RETLY

FIG. 7

ZNF206 Isoform 1
Sequence 2568 bp

ATGCTTGGAGAATCAGTCCCAGCTGCCCTGGAGCAGGAGCAGCTGGGGGAAGTCAAGCTGGAGGAGGA
GGAGGCTGTCAGCCCAGAGGACCCCAGGCGACCAGAGTCCAGGCTGAGGCCCGAGGTGGCTCACCAGC
TGTTCAGATGCTTCCAGTATCAGGAGGACATGGGGCCACGGGCGTCCCTGAGCCGGCTCCGGGAGCTCT
GCGGCCACTGGCTGCGGCCGGCTCTGCACACCAAGAAACAGATCCTGGAGCTGCTGGTGCTGGAGCAGT
TCCTGAGTGTGCTGCCTCCGCACCTCCTGGGCCGCCTGCAGGGGCAGCCGCTCAGGGATGGGGAGGAGG
TGGTGCTGCTGCTCGAGGGCATCCACCGGGAGCCCAGCCACGCGGGGCCGCTGGTGAGAGGGTGGGGC
AGCGGGCTGAGCAGCATGCGGATGATGGGGACTTGATCCCCCAGTGAGGAATCTCTGGAAACTCCACT
TTCCCCCACCTGACCATTCCTTCTTCACCTCCTAACTCCTCCCCTGGCTGACTCTAACCTCGTTTCTGTCCC
ATGTCCCCTCGGAGTCAGGACACAGGTTGCCACCCCGGGAGTCACTTAACTTGAATGTGTTTTGAACAG
GATTTTAGTTGTAATGCTGGCAAGAGTTGTCCCCGTGCAGACGTCACCTTGGAGGAAAAGGGGTGTGCTT
CCCAGGTCCCCAGCCACAGCCCCAAGAAGGAATTGCCTGCGGAAGAGCCTTCAGTGCTGGGCCCATCGG
ATGAGCCTCCCCGACCCCAGCCAAGGGCTGCCCAGCCTGCTGAGCCGGGACAGTGGAGGCTTCCCCCAA
GTTCAAAGCAGCCGCTGAGCCCGGGGCCCCAGAAGACATTCCAGGCCCTGCAAGAAAGCAGTCCCCAG
GGCCCCTCACCATGGCCAGAGGAGAGTTCCCGAGATCAGGAGCTGGCGGCTGTGCTGGAGTGCCTGACC
TTTGAGGATGTGCCAGAGAATAAGGCGTGGCCTGCACACCCCTGGGATTCGGAAGCAGAACCCCAGAC
AAGGAGGAATTTAAACAAGAAGAGCCCAAAGGGGCTGCCTGGCCCACTCCCATCTTAGCAGAGTCCCA
GGCAGATAGTCCTGGGGTGCCGGGAGAGCCTTGCGCCCAGTCGCTCGGACGGGGCGCTGCGGCTAGCGG
CCCTGGCGAAGATGGGTCCCTTCTTGGCAGCAGTGAAATTTTGGAGGTCAAAGTGGCTGAGGGCGTCCC
CGAGCCCAATCCGGAGTTGCAGTTCATCTGCGCGGACTGCGGGGTGAGCTTCCCGCAGCTGTCTCGCCTG
AAGGCGCACCAGCTGCGCTCGCACCCGGCTGGGCGCTCCTTCCTGTGCCTTTGCTGCGGGAAGAGCTTCG
GCCGCAGCTCCATTCTCAAGCTGCACATGCGCACTCACACGGACGAGCGGCCGCACGCCTGCCACCTGT
GCGGCCACCGCTTCCGCCAGAGCTCGCACCTGAGCAAGCACCTGCTGACCCACTCCTCCGAACCCGCCTT
CCTGTGCGCAGAGTGCGGCCGCGGCTTCCAGCGCCGCGCCAGCCTTGTGCAGCACCTGCTGGCGCACGC
CCAGGACCAGAAGCCGCCCTGCGCTCCTGAGAGTAAGGCCGAAGCGCCGCCACTGACCGATGTCCTGTG
CTCCCACTGCGGCCAGAGCTTCCAGCGCCGCTCCAGCCTCAAGCGCCACCTGCGGATCCACGCCAGGGA
CAAGGACCGCCGGTCCTCCGAAGGCTCCGGCAGCCGCCGCCGGGACTCCGACCGGAGGCCCTTCGTGTG
CAGCGACTGCGGCAAGGCCTTCCGGCGCAGCGAGCACCTGGTGGCCCACCGGAGGGTGCACACGGGCG
AGCGGCCCTTCTCCTGCCAGGCTTGCGGCCGCAGCTTCACGCAGAGCTCGCAGCTGGTCAGCCACCAAC
GGGTGCACACGGGCGAGAAGCCCTACGCCTGTCCGCAGTGCGGGAAGCGCTTTGTGCGCCGGGCCAGCC
TTGCCCGCCACCTGCTGACCCACGGTGGCCCTCGGCCCCACCACTGCACCCAGTGCGGGAAGAGTTTCG
GCCAGACCCAGGATCTGGCCCCGCCACCAGCGCAGCCACACGGGCGAGAAGCCCTGCCGCTGCAGCGAG
TGCGGTGAGGGCTTCAGCCAGAGCGCCCACCTGGCGCGCCACCAGCGCATCCACACAGGGGAGAAGCC
CCACGCCTGCGACACCTGCGGCCACCGTTTCCGCAATAGCTCCAACCTGGCCCGCCATCGCCGCAGCCA
CACGGGCGAGCGGCCCTACAGCTGTCAGACGTGCGGTCGCAGCTTCCGGCGCAACGCGCATCTGCGGCG
GCACCTGGCTACCCATGCGGAGCCCGGGCAGGAGCAGGCCGAGCCCCCGCAGGAGTGCGTGGAGTGCG
GGAAGAGCTTCAGCCGCAGCTGCAATCTGCTGCGACACCTGCTGGTGCACACGGGCGCCAGGCCCTACT
CCTGCACGCAGTGTGGCCGCAGCTTCAGCCGCAACTCCCACCTGCTGCGCCACCTGCGCACCCACGCCC
GCGAGACGCTGTACTAG

FIG. 10

ZNF206 Isoform 2
Sequence 2343bp

ATGCTTGGAGAATCAGTCCCAGCTGCCCTGGAGCAGGAGCAGCTGGGGGAAGTCAAGCTGGAGGAGGA
GGAGGCTGTCAGCCCAGAGGACCCCAGGCGACCAGAGTCCAGGCTGAGGCCCGAGGTGGCTCACCAGC
TGTTCAGATGCTTCCAGTATCAGGAGGACATGGGGCCACGGGCGTCCCTGAGCCGGCTCCGGGAGCTCT
GCGGCCACTGGCTGCGGCCGGCTCTGCACACCAAGAAACAGATCCTGGAGCTGCTGGTGCTGGAGCAGT
TCCTGAGTGTGCTGCCTCCGCACCTCCTGGGCCGCCTGCAGGGGCAGCCGCTCAGGGATGGGGAGGAGG
TGGTGCTGCTGCTCGAGGGCATCCACCGGGAGCCCAGCCACGCGGGGCCGCTGGATTTTAGTTGTAATG
CTGGCAAGAGTTGTCCCCGTGCAGACGTCACCTTGGAGGAAAAGGGGTGTGCTTCCCAGGTCCCCAGCC
ACAGCCCCAAGAAGGAATTGCCTGCGGAAGAGCCTTCAGTGCTGGGCCCATCGGATGAGCCTCCCCGAC
CCCAGCCAAGGGCTGCCCAGCCTGCTGAGCCGGGACAGTGGAGGCTTCCCCCAAGTTCAAAGCAGCCGC
TGAGCCCGGGGCCCCAGAAGACATTCCAGGCCCTGCAAGAAAGCAGTCCCCAGGGCCCCTCACCATGGC
CAGAGGAGAGTTCCCGAGATCAGGAGCTGGCGGCTGTGCTGGAGTGCCTGACCTTTGAGGATGTGCCAG
AGAATAAGGCGTGGCCTGCACACCCCCTGGGATTCGGAAGCAGAACCCCAGACAAGGAGGAATTTAAA
CAAGAAGAGCCCAAAGGGGCTGCCTGGCCCACTCCCATCTTAGCAGAGTCCCAGGCAGATAGTCCTGGG
GTGCCGGGAGAGCCTTGCGCCCAGTCGCTCGGACGGGGCGCTGCGGCTAGCGGCCCTGGCGAAGATGG
GTCCCTTCTTGGCAGCAGTGAAATTTTGGAGGTCAAAGTGGCTGAGGGCGTCCCCGAGCCCAATCCGGA
GTTGCAGTTCATCTGCGCGGACTGCGGGGTGAGCTTCCCGCAGCTGTCTCGCCTGAAGGCGCACCAGCT
GCGCTCGCACCCGGCTGGGCGCTCCTTCCTGTGCCTTTGCTGCGGGAAGAGCTTCGGCCGCAGCTCCATT
CTCAAGCTGCACATGCGCACTCACACGGACGAGCGGCCGCACGCCTGCCACCTGTGCGGCCACCGCTTC
CGCCAGAGCTCGCACCTGAGCAAGCACCTGCTGACCCACTCCTCCGAACCCGCCTTCCTGTGCGCAGAG
TGCGGCCGCGGCTTCCAGCGCCGCGCCAGCCTTGTGCAGCACCTGCTGGCGCACGCCCAGGACCAGAAG
CCGCCCTGCGCTCCTGAGAGTAAGGCCGAAGCGCCGCCACTGACCGATGTCCTGTGCTCCCACTGCGGC
CAGAGCTTCCAGCGCCGCTCCAGCCTCAAGCGCCACCTGCGGATCCACGCCAGGGACAAGGACCGCCGG
TCCTCCGAAGGCTCCGGCAGCCGCCGCCGGGACTCCGACCGGAGGCCCTTCGTGTGCAGCGACTGCGGC
AAGGCCTTCCGGCGCAGCGAGCACCTGGTGGCCCACCGGAGGGTGCACACGGGCGAGCGGCCCTTCTCC
TGCCAGGCTTGCGGCCGCAGCTTCACGCAGAGCTCGCAGCTGGTCAGCCACCAACGGGTGCACACGGGC
GAGAAGCCCTACGCCTGTCCGCAGTGCGGGAAGCGCTTTGTGCGCCGGGCCAGCCTTGCCCGCCACCTG
CTGACCCACGGTGGCCCTCGGCCCCACCACTGCACCCAGTGCGGGAAGAGTTTCGGCCAGACCCAGGAT
CTGGCCCGCCACCAGCGCAGCCACACGGGCGAGAAGCCCTGCCGCTGCAGCGAGTGCGGTGAGGGCTTC
AGCCAGAGCGCCCACCTGGCGCGCCACCAGCGCATCCACACAGGGGAGAAGCCCCACGCCTGCGACAC
CTGCGGCCACCGTTTCCGCAATAGCTCCAACCTGGCCCGCCATCGCCGCAGCCACACGGGCGAGCGGCC
CTACAGCTGTCAGACGTGCGGTCGCAGCTTCCGGCGCAACGCGCATCTGCGGCGGCACCTGGCTACCCA
TGCGGAGCCCGGGCAGGAGCAGGCCGAGCCCCCGCAGGAGTGCGTGGAGTGCGGGAAGAGCTTCAGCC
GCAGCTGCAATCTGCTGCGACACCTGCTGGTGCACACGGGCGCCAGGCCCTACTCCTGCACGCAGTGTG
GCCGCAGCTTCAGCCGCAACTCCCACCTGCTGCGCCACCTGCGCACCCACGCCCGCGAGACGCTGTACT
AG

FIG. 10 *(Continued)*

ZNF206 Isoform 3
Sequence 2175 bp

ATGCTTGGAGAATCAGTCCCAGCTGCCCTGGAGCAGGAGCAGCTGGGGGAAGTCAAGCTGGAGGAGGA
GGAGGCTGTCAGCCCAGAGGACCCCAGGCGACCAGAGTCCAGGCTGAGGCCCGAGGTGGCTCACCAGC
TGTTCAGATGCTTCCAGTATCAGGAGGACATGGGGCCACGGGCGTCCCTGAGCCGGCTCCGGGAGCTCT
GCGGCCACTGGCTGCGGCCGGCTCTGCACACCAAGAAACAGATCCTGGAGCTGCTGGTGCTGGAGCAGT
TCCTGAGTGTGCTGCCTCCGCACCTCCTGGGCCGCCTGCAGGGGCAGCCGCTCAGGGATGGGGAGGAGG
TGGTGCTGCTGCTCGAGGGCATCCACCGGGAGCCCAGCCACGCGGGGCCGCTGGATTTTAGTTGTAATG
CTGGCAAGAGTTGTCCCCGTGCAGACGTCACCTTGGAGGAAAAGGGGTGTGCTTCCCAGGTCCCCAGCC
ACAGCCCCAAGAAGGAATTGCCTGCGGAAGAGCCTTCAGTGCTGGGCCCATCGGATGAGCCTCCCCGAC
CCCAGCCAAGGGCTGCCCAGCCTGCTGAGCCGGGACAGTGGAGGCTTCCCCCAAGTTCAAAGCAGCCGC
TGAGCCCGGGGCCCCAGAAGACATTCCAGGCCCTGCAAGAAAGCAGTCCCCAGGGCCCCTCACCATGGC
CAGAGGAGAGTTCCCGAGATCAGGAGCTGGCGGCTGTGCTGGAGTGCCTGACCTTTGAGGATGTGCCAG
AGAATAAGGCGTGGCCTGCACACCCCCTGGGATTCGGAAGCAGAACCCCAGACAAGGAGGAATTTAAA
CAAGAAGAGCCCAAAGGGGCTGCCTGGCCCACTCCCATCTTAGCAGAGTCCCAGGCAGATAGTCCTGGG
GTGCCGGGAGAGCCTTGCGCCCAGTCGCTCGGACGGGGCGCTGCGGCTAGCGGCCCTGGTGAAGATGGG
TCCCTTCTTGGCAGCAGTGAAATTTTGGAGGTCAAAGTGGCTGAGGGCGTCCCCGAGCCCAATCCGGAG
TTGCAGTTCATCTGCGCGGACTGCGGGGTGAGCTTCCCGCAGCTGTCTCGCCTGAAGGCGCACCAGCTGC
GCTCGCACCCGGCTGGGCGCTCCTTCCTGTGCCTTTGCTGCGGGAAGAGCTTCGGCCGCAGCTCCATTCT
CAAGCTGCACATGCGCACTCACACGGACGAGCGGCCGCACGCCTGCCACCTGTGCGGCCACCGCTTCCG
CCAGAGCTCGCACCTGAGCAAGCACCTGCTGACCCACTCCTCCGAACCCGCCTTCCTGTGCGCAGAGTG
CGGCCGCGGCTTCCAGCGCCGCGCCAGCCTTGTGCAGCACCTGCTGGCGCACGCCCAGGACCAGAAGCC
GCCCTGCGCTCCTGAGAGTAAGGCCGAAGCGCCGCCACTGACCGATGTCCTGTGCTCCCACTGCGGCCA
GAGCTTCCAGCGCCGCTCCAGCCTCAAGCGCCACCTGCGGATCCACGCCAGGGACAAGGACCGCCGGTC
CTCCGAAGGCTCCGGCAGCCGCCGCCGGGACTCCGACCGGAGGCCCTTCGTGTGCAGCGACTGCGGCAA
GGCCTTCCGGCGCAGCGAGCACCTGGTGGCCCACCGGAGGGTGCACACGGGCGAGCGGCCCTTCTCCTG
CCAGGCTTGCGGCCGCAGCTTCACGCAGAGCTCGCAGCTGGTCAGCCACCAACGGGTGCACACGGGCGA
GAAGCCCTACGCCTGTCCGCAGTGCGGGAAGCGCTTTGTGCGCCGGGCCAGCCTTGCCCGCCACCTGCT
GACCCACGGTGGCCCTCGGCCCCACCACTGCACCCAGTGCGGGAAGAGTTTCGGCCAGACCCAGGATCT
GGCTCGCCACCAGCGCAGCCACACGGGCGAGCGGCCCTACAGCTGTCAGACGTGCGGTCGCAGCTTCCG
GCGCAACGCGCATCTGCGGCGGCACCTGGCTACCCATGCGGAGCCCGGGCAGGAGCAGGCCGAGCCCC
CGCAGGAGTGCGTGGGGTGCGGGAAGAGCTTCAGCCGCAGCTGCAATCTGCTGCGACACCTGCTGGTGC
ACACGGGCGCCAGGCCCTACTCCTGCACGCAGTGTGGCCGCAGCTTCAGCCGCAACTCCCACCTGCTGC
GCCACCTGCGCACCCACGCCCGCGAGACGCTGTACTAG

FIG. 10 (Continued)

ZNF206 isoform 4
Sequence 2075 bp

ATGCTTGGAGAATCAGTCCCAGCTGCCCTGGAGCAGGAGCAGCTGGGGGAAGTCAAGCTGGAGGAGGA
GGAGGCTGTCAGCCCAGAGGACCCCAGGCGACCAGAGTCCAGGCTGAGGCCCGAGGTGGCTCACCAGC
TGTTCAGATGCTTCCAGTATCAGGAGGACATGGGGCCACGGGCGTCCCTGAGCCGGCTCCGGGAGCTCT
GCGGCCACTGGCTGCGGCCGGCTCTGCACACCAAGAAACAGATCCTGGAGCTGCTGGTGCTGGAGCAGT
TCCTGAGTGTGCTGCCTCCGCACCTCCTGGGCCGCCTGCAGGGGCAGCCGCTCAGGGATGGGGAGGAGG
TGGTGCTGCTGCTCGAGGGCATCCACCGGGAGCCCAGCCACGCGGGGCCGCTGGTCCCCAGGGCCCCTC
ACCATGGCCAGAGGAGAGTTCCCGAGATCAGGAGCTGGCGGCTGTGCTGGAGTGCCTGACCTTTGAGGA
TGTGCCAGAGAATAAGGCGTGGCCTGCACACCCCCTGGGATTCGGAAGCAGAACCCCAGACAAGGAGG
AATTTAAACAAGAAGAGCCCAAAGGGGCTGCCTGGCCCACTCCCATCTTAGCAGAGTCCCAGGCAGATA
GTCCTGGGGTGCCGGGAGAGCCTTGCGCCCAGTCGCTCGGACGGGGCGCTGCGGCTAGCGGCCCTGGCG
AAGATGGGTCCCTTCTTGGCAGCAGTGAAATTTTGGAGGTCAAAGTGGCTGAGGGCGTCCCCGAGCCCA
ATCCGGAGTTGCAGTTCATCTGCGCGGACTGCGGGGTGAGCTTCCCGCAGCTGTCTCGCCTGAAGGCGC
ACCAGCTGCGCTCGCACCCGGCTGGGCGCTCCTTCCTGTGCCTTTGCTGCGGGAAGAGCTTCGGCCGCAG
CTCCATTCTCAAGCTGCACATGCGCACTCACACGGACGAGCGGCCGCACGCCTGCCACCTGTGCGGCCA
CCGCTTCCGCCAGAGCTCGCACCTGAGCAAGCACCTGCTGACCCACTCCTCCGAACCCGCCTTCCTGTGC
GCAGAGTGCGGCCGCGGCTTCCAGCGCCGCGCCAGCCTTGTGCAGCACCTGCTGGCGCACGCCCAGGAC
CAGAAGCCGCCCTGCGCTCCTGAGAGTAAGGCCGAAGCGCCGCCACTGACCGATGTCCTGTGCTCCCAC
TGCGGCCAGAGCTTCCAGCGCCGCTCCAGCCTCAAGCGCCACCTGCGGATCCACGCCAGGGACAAGGAC
CGCCGGTCCTCCGAAGGCTCCGGCAGCCGCCGCCGGGACTCCGACCGGAGGCCCTTCGTGTGCAGCGAC
TGCGGCAAGGCCTTCCGGCGCAGCGAGCACCTGGTGGCCCACCGGAGGGTGCACACGGGCGAGCGGCC
CTTCTCCTGCCAGGCTTGCGGCCGCAGCTTCACGCAGAGCTCGCAGCTGGTCAGCCACCAACGGGTGCA
CACGGGCGAGAAGCCCTACGCCTGTCCGCAGTGCGGGAAGCGCTTTGTGCGCCGGGCCAGCCTTGCCCG
CCACCTGCTGACCCACGGTGGCCCTCGGCCCCACCACTGCACCCAGTGCGGGAAGAGTTTCGGCCAGAC
CCAGGATCTGGCCCGCCACCAGCGCAGCCACACGGGCGAGAAGCCCTGCCGCTGCAGCGAGTGCGGTG
AGGGCTTCAGCCAGAGCGCCCACCTGGCGCGCCACCAGCGCATCCACACAGGGGAGAAGCCCCACGCC
TGCGACACCTGCGGCCACCGTTTCCGCAATAGCTCCAACCTGGCCCGCCATCGCCGCAGCCACACGGGC
GAGCGGCCCTACAGCTGTCAGACGTGCGGTCGCAGCTTCCGGCGCAACGCGCATCTGCGGCGGCACCTG
GCTACCCATGCGGAGCCCGGGCAGGAGCAGGCCGAGCCCCGCAGGAGTGCGTGGAGTGCGGGAAGAG
CTTCAGCCGCAGCTGCAATCTGCTGCGACACCTGCTGGTGCACACGGGCGCCAGGCCCTACTCCTGCAC
GCAGTGTGGCCGCAGCTTCAGCCGCAACTCCCACCTGCTGCGCCACCTGCGCACCCACGCCCGCGAGAC
GCTGTACTAG

FIG. 10 (Continued)

SEQUENCE LISTING

```
<160> NUMBER OF SEQ ID NOS: 37

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttgaagaag agacccgat                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttctgcacg ctccactac                                                  19

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acacgggagt gcatctacta caacg                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

```
ttcatgagct gggccttcca gacac                                         25
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
agaacctgtc acaagctgtg                                               20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
cacagcaagc tgaggatgtc                                               20
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tggcaccaca cctttctaca atgagc                                        26
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gcacagcttc tccttaatgt cacgc                                         25
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gaacctgtgc gagtggatgc g                                             21
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
ggtctatggc tgtgggtggg ag                                            22
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcttacctt accatcgacc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctccagagca tggtacatgg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
catcaagacg gagcctggcc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgactgtcgg ccaagaccag                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcttggttct cgttgagtgg                                              20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caggagctta tagggctca gac                                           23

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtaagctgc acatggaagg                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
attgtggctc aattctgtgc                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccgcatgtac aacatgatgg                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttcttcatg agcgtcttgg                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccatgactcc aacttccacc                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acggaggacg tgacttcggc                                                   20

<210> SEQ ID NO 23
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggcaaacaac ccacttctgc                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgttccaggc ctgattgttc                                                   20

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgtgaagctg gagaaggaga agctg                                             25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caagggccgc agcttacaca tgttc                                             25

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcacggaat ttgaacagta                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggatcaggga cctgtcacac                                                   20

<210> SEQ ID NO 29
<211> LENGTH: 148
<212> TYPE: PRT
<213> ORGANISM: Homo sapiens
```

<400> SEQUENCE: 29

Met Leu Gly Glu Ser Val Pro Ala Ala Leu Glu Gln Glu Gln Leu Gly
1               5                   10                  15

Glu Val Lys Leu Glu Glu Glu Ala Val Ser Pro Glu Asp Pro Arg
            20                  25                  30

Arg Pro Glu Ser Arg Leu Arg Pro Glu Val Ala His Gln Leu Phe Arg
        35                  40                  45

Cys Phe Gln Tyr Gln Glu Asp Met Gly Pro Arg Ala Ser Leu Ser Arg
    50                  55                  60

Leu Arg Glu Leu Cys Gly His Trp Leu Arg Pro Ala Leu His Thr Lys
65                  70                  75                  80

Lys Gln Ile Leu Glu Leu Leu Val Leu Glu Gln Phe Leu Ser Val Leu
                85                  90                  95

Pro Pro His Leu Leu Gly Arg Leu Gln Gly Gln Pro Leu Arg Asp Gly
            100                 105                 110

Glu Glu Val Val Leu Leu Glu Gly Ile His Arg Glu Pro Ser His
        115                 120                 125

Ala Gly Pro Leu Val Arg Gly Trp Gly Ser Gly Leu Ser Ser Met Arg
    130                 135                 140

Met Met Gly Thr
145

<210> SEQ ID NO 30
<211> LENGTH: 780
<212> TYPE: PRT
<213> ORGANISM: Homo sapiens

<400> SEQUENCE: 30

Met Leu Gly Glu Ser Val Pro Ala Ala Leu Glu Gln Glu Gln Leu Gly
1               5                   10                  15

Glu Val Lys Leu Glu Glu Glu Ala Val Ser Pro Glu Asp Pro Arg
            20                  25                  30

Arg Pro Glu Ser Arg Leu Arg Pro Glu Val Ala His Gln Leu Phe Arg
        35                  40                  45

Cys Phe Gln Tyr Gln Glu Asp Met Gly Pro Arg Ala Ser Leu Ser Arg
    50                  55                  60

Leu Arg Glu Leu Cys Gly His Trp Leu Arg Pro Ala Leu His Thr Lys
65                  70                  75                  80

Lys Gln Ile Leu Glu Leu Leu Val Leu Glu Gln Phe Leu Ser Val Leu
                85                  90                  95

Pro Pro His Leu Leu Gly Arg Leu Gln Gly Gln Pro Leu Arg Asp Gly
            100                 105                 110

Glu Glu Val Val Leu Leu Glu Gly Ile His Arg Glu Pro Ser His
        115                 120                 125

Ala Gly Pro Leu Asp Phe Ser Cys Asn Ala Gly Lys Ser Cys Pro Arg
    130                 135                 140

Ala Asp Val Thr Leu Glu Glu Lys Gly Cys Ala Ser Gln Val Pro Ser
145                 150                 155                 160

His Ser Pro Lys Lys Glu Leu Pro Ala Glu Glu Pro Ser Val Leu Gly
            165                 170                 175

Pro Ser Asp Glu Pro Pro Arg Pro Gln Pro Arg Ala Ala Gln Pro Ala
        180                 185                 190

Glu Pro Gly Gln Trp Arg Leu Pro Pro Ser Ser Lys Gln Pro Leu Ser
    195                 200                 205

-continued

```
Pro Gly Pro Gln Lys Thr Phe Gln Ala Leu Gln Glu Ser Ser Pro Gln
    210             215                 220

Gly Pro Ser Pro Trp Pro Glu Glu Ser Ser Arg Asp Gln Glu Leu Ala
225             230                 235                 240

Ala Val Leu Glu Cys Leu Thr Phe Glu Asp Val Pro Glu Asn Lys Ala
                245                 250                 255

Trp Pro Ala His Pro Leu Gly Phe Gly Ser Arg Thr Pro Asp Lys Glu
            260                 265                 270

Glu Phe Lys Gln Glu Glu Pro Lys Gly Ala Ala Trp Pro Thr Pro Ile
        275                 280                 285

Leu Ala Glu Ser Gln Ala Asp Ser Pro Gly Val Pro Gly Glu Pro Cys
    290                 295                 300

Ala Gln Ser Leu Gly Arg Gly Ala Ala Ser Gly Pro Gly Glu Asp
305                 310                 315                 320

Gly Ser Leu Leu Gly Ser Ser Glu Ile Leu Glu Val Lys Val Ala Glu
                325                 330                 335

Gly Val Pro Glu Pro Asn Pro Glu Leu Gln Phe Ile Cys Ala Asp Cys
            340                 345                 350

Gly Val Ser Phe Pro Gln Leu Ser Arg Leu Lys Ala His Gln Leu Arg
        355                 360                 365

Ser His Pro Ala Gly Arg Ser Phe Leu Cys Leu Cys Cys Gly Lys Ser
    370                 375                 380

Phe Gly Arg Ser Ser Ile Leu Lys Leu His Met Arg Thr His Thr Asp
385                 390                 395                 400

Glu Arg Pro His Ala Cys His Leu Cys Gly His Arg Phe Arg Gln Ser
                405                 410                 415

Ser His Leu Ser Lys His Leu Leu Thr His Ser Ser Glu Pro Ala Phe
            420                 425                 430

Leu Cys Ala Glu Cys Gly Arg Gly Phe Gln Arg Arg Ala Ser Leu Val
        435                 440                 445

Gln His Leu Leu Ala His Ala Gln Asp Gln Lys Pro Pro Cys Ala Pro
    450                 455                 460

Glu Ser Lys Ala Glu Ala Pro Pro Leu Thr Asp Val Leu Cys Ser His
465                 470                 475                 480

Cys Gly Gln Ser Phe Gln Arg Arg Ser Ser Leu Lys Arg His Leu Arg
                485                 490                 495

Ile His Ala Arg Asp Lys Asp Arg Arg Ser Glu Gly Ser Gly Ser
            500                 505                 510

Arg Arg Arg Asp Ser Asp Arg Arg Pro Phe Val Cys Ser Asp Cys Gly
        515                 520                 525

Lys Ala Phe Arg Arg Ser Glu His Leu Val Ala His Arg Arg Val His
    530                 535                 540

Thr Gly Glu Arg Pro Phe Ser Cys Gln Ala Cys Gly Arg Ser Phe Thr
545                 550                 555                 560

Gln Ser Ser Gln Leu Val Ser His Gln Arg Val His Thr Gly Glu Lys
                565                 570                 575

Pro Tyr Ala Cys Pro Gln Cys Gly Lys Arg Phe Val Arg Ala Ser
            580                 585                 590

Leu Ala Arg His Leu Leu Thr His Gly Gly Pro Arg Pro His His Cys
        595                 600                 605

Thr Gln Cys Gly Lys Ser Phe Gly Gln Thr Gln Asp Leu Ala Arg His
    610                 615                 620

Gln Arg Ser His Thr Gly Glu Lys Pro Cys Arg Cys Ser Glu Cys Gly
625                 630                 635                 640
```

Glu Gly Phe Ser Gln Ser Ala His Leu Ala Arg His Gln Arg Ile His
                645                 650                 655

Thr Gly Glu Lys Pro His Ala Cys Asp Thr Cys Gly His Arg Phe Arg
            660                 665                 670

Asn Ser Ser Asn Leu Ala Arg His Arg Arg Ser His Thr Gly Glu Arg
        675                 680                 685

Pro Tyr Ser Cys Gln Thr Cys Gly Arg Ser Phe Arg Arg Asn Ala His
    690                 695                 700

Leu Arg Arg His Leu Ala Thr His Ala Glu Pro Gly Gln Gln Ala
705                 710                 715                 720

Glu Pro Pro Gln Glu Cys Val Glu Cys Gly Lys Ser Phe Ser Arg Ser
                725                 730                 735

Cys Asn Leu Leu Arg His Leu Leu Val His Thr Gly Ala Arg Pro Tyr
            740                 745                 750

Ser Cys Thr Gln Cys Gly Arg Ser Phe Ser Arg Asn Ser His Leu Leu
        755                 760                 765

Arg His Leu Arg Thr His Ala Arg Glu Thr Leu Tyr
770                 775                 780

<210> SEQ ID NO 31
<211> LENGTH: 724
<212> TYPE: PRT
<213> ORGANISM: Homo sapiens

<400> SEQUENCE: 31

Met Leu Gly Glu Ser Val Pro Ala Ala Leu Glu Gln Glu Gln Leu Gly
1               5                   10                  15

Glu Val Lys Leu Glu Glu Glu Ala Val Ser Pro Glu Asp Pro Arg
            20                  25                  30

Arg Pro Glu Ser Arg Leu Arg Pro Glu Val Ala His Gln Leu Phe Arg
        35                  40                  45

Cys Phe Gln Tyr Gln Glu Asp Met Gly Pro Arg Ala Ser Leu Ser Arg
    50                  55                  60

Leu Arg Glu Leu Cys Gly His Trp Leu Arg Pro Ala Leu His Thr Lys
65                  70                  75                  80

Lys Gln Ile Leu Glu Leu Leu Val Leu Glu Gln Phe Leu Ser Val Leu
                85                  90                  95

Pro Pro His Leu Leu Gly Arg Leu Gln Gly Gln Pro Leu Arg Asp Gly
            100                 105                 110

Glu Glu Val Val Leu Leu Leu Glu Gly Ile His Arg Glu Pro Ser His
        115                 120                 125

Ala Gly Pro Leu Asp Phe Ser Cys Asn Ala Gly Lys Ser Cys Pro Arg
    130                 135                 140

Ala Asp Val Thr Leu Glu Glu Lys Gly Cys Ala Ser Gln Val Pro Ser
145                 150                 155                 160

His Ser Pro Lys Lys Glu Leu Pro Ala Glu Pro Ser Val Leu Gly
                165                 170                 175

Pro Ser Asp Glu Pro Arg Pro Gln Pro Arg Ala Ala Gln Pro Ala
            180                 185                 190

Glu Pro Gly Gln Trp Arg Leu Pro Ser Ser Lys Gln Pro Leu Ser
        195                 200                 205

Pro Gly Pro Gln Lys Thr Phe Gln Ala Leu Gln Glu Ser Ser Pro Gln
    210                 215                 220

Gly Pro Ser Pro Trp Pro Glu Glu Ser Ser Arg Asp Gln Glu Leu Ala
225                 230                 235                 240

```
Ala Val Leu Glu Cys Leu Thr Phe Glu Asp Val Pro Glu Asn Lys Ala
                245                 250                 255
Trp Pro Ala His Pro Leu Gly Phe Gly Ser Arg Thr Pro Asp Lys Glu
                260                 265                 270
Glu Phe Lys Gln Glu Pro Lys Gly Ala Ala Trp Pro Thr Pro Ile
        275                 280                 285
Leu Ala Glu Ser Gln Ala Asp Ser Pro Gly Val Pro Gly Glu Pro Cys
290                 295                 300
Ala Gln Ser Leu Gly Arg Gly Ala Ala Ser Gly Pro Gly Glu Asp
305                 310                 315                 320
Gly Ser Leu Leu Gly Ser Ser Glu Ile Leu Glu Val Lys Val Ala Glu
                325                 330                 335
Gly Val Pro Glu Pro Asn Pro Glu Leu Gln Phe Ile Cys Ala Asp Cys
                340                 345                 350
Gly Val Ser Phe Pro Gln Leu Ser Arg Leu Lys Ala His Gln Leu Arg
                355                 360                 365
Ser His Pro Ala Gly Arg Ser Phe Leu Cys Leu Cys Cys Gly Lys Ser
        370                 375                 380
Phe Gly Arg Ser Ser Ile Leu Lys Leu His Met Arg Thr His Thr Asp
385                 390                 395                 400
Glu Arg Pro His Ala Cys His Leu Cys Gly His Arg Phe Arg Gln Ser
                405                 410                 415
Ser His Leu Ser Lys His Leu Leu Thr His Ser Ser Glu Pro Ala Phe
                420                 425                 430
Leu Cys Ala Glu Cys Gly Arg Gly Phe Gln Arg Arg Ala Ser Leu Val
        435                 440                 445
Gln His Leu Leu Ala His Ala Gln Asp Gln Lys Pro Pro Cys Ala Pro
    450                 455                 460
Glu Ser Lys Ala Glu Ala Pro Pro Leu Thr Asp Val Leu Cys Ser His
465                 470                 475                 480
Cys Gly Gln Ser Phe Gln Arg Arg Ser Ser Leu Lys Arg His Leu Arg
                485                 490                 495
Ile His Ala Arg Asp Lys Asp Arg Arg Ser Ser Glu Gly Ser Gly Ser
                500                 505                 510
Arg Arg Arg Asp Ser Asp Arg Arg Pro Phe Val Cys Ser Asp Cys Gly
        515                 520                 525
Lys Ala Phe Arg Arg Ser Glu His Leu Val Ala His Arg Arg Val His
    530                 535                 540
Thr Gly Glu Arg Pro Phe Ser Cys Gln Ala Cys Gly Arg Ser Phe Thr
545                 550                 555                 560
Gln Ser Ser Gln Leu Val Ser His Gln Arg Val His Thr Gly Glu Lys
                565                 570                 575
Pro Tyr Ala Cys Pro Gln Cys Gly Lys Arg Phe Val Arg Ala Ser
                580                 585                 590
Leu Ala Arg His Leu Leu Thr His Gly Gly Pro Arg Pro His His Cys
        595                 600                 605
Thr Gln Cys Gly Lys Ser Phe Gly Gln Thr Gln Asp Leu Ala Arg His
    610                 615                 620
Gln Arg Ser His Thr Gly Glu Arg Pro Tyr Ser Cys Gln Thr Cys Gly
625                 630                 635                 640
Arg Ser Phe Arg Arg Asn Ala His Leu Arg Arg His Leu Ala Thr His
                645                 650                 655
Ala Glu Pro Gly Gln Glu Gln Ala Glu Pro Pro Gln Glu Cys Val Gly
```

```
                        660                 665                 670
Cys Gly Lys Ser Phe Ser Arg Ser Cys Asn Leu Leu Arg His Leu Leu
            675                 680                 685

Val His Thr Gly Ala Arg Pro Tyr Ser Cys Thr Gln Cys Gly Arg Ser
        690                 695                 700

Phe Ser Arg Asn Ser His Leu Leu Arg His Leu Arg Thr His Ala Arg
705                 710                 715                 720

Glu Thr Leu Tyr

<210> SEQ ID NO 32
<211> LENGTH: 156
<212> TYPE: PRT
<213> ORGANISM: Homo sapiens

<400> SEQUENCE: 32

Met Leu Gly Glu Ser Val Pro Ala Ala Leu Glu Gln Glu Gln Leu Gly
1               5                   10                  15

Glu Val Lys Leu Glu Glu Glu Ala Val Ser Pro Glu Asp Pro Arg
            20                  25                  30

Arg Pro Glu Ser Arg Leu Arg Pro Glu Val Ala His Gln Leu Phe Arg
        35                  40                  45

Cys Phe Gln Tyr Gln Glu Asp Met Gly Pro Arg Ala Ser Leu Ser Arg
    50                  55                  60

Leu Arg Glu Leu Cys Gly His Trp Leu Arg Pro Ala Leu His Thr Lys
65                  70                  75                  80

Lys Gln Ile Leu Glu Leu Leu Val Leu Glu Gln Phe Leu Ser Val Leu
                85                  90                  95

Pro Pro His Leu Leu Gly Arg Leu Gln Gly Gln Pro Leu Arg Asp Gly
            100                 105                 110

Glu Glu Val Val Leu Leu Glu Gly Ile His Arg Glu Pro Ser His
        115                 120                 125

Ala Gly Pro Leu Val Pro Arg Ala Pro His His Gly Gln Arg Arg Val
    130                 135                 140

Pro Glu Ile Arg Ser Trp Arg Leu Cys Trp Ser Ala
145                 150                 155

<210> SEQ ID NO 33
<211> LENGTH: 780
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Leu Gly Glu Ser Val Pro Ala Ala Leu Glu Gln Glu Gln Leu Gly
1               5                   10                  15

Glu Val Lys Leu Glu Glu Glu Ala Val Ser Pro Glu Asp Pro Arg
            20                  25                  30

Arg Pro Glu Ser Arg Leu Arg Pro Glu Val Ala His Gln Leu Phe Arg
        35                  40                  45

Cys Phe Gln Tyr Gln Glu Asp Met Gly Pro Arg Ala Ser Leu Ser Arg
    50                  55                  60

Leu Arg Glu Leu Cys Gly His Trp Leu Arg Pro Ala Leu His Thr Lys
65                  70                  75                  80

Lys Gln Ile Leu Glu Leu Leu Val Leu Glu Gln Phe Leu Ser Val Leu
                85                  90                  95
```

-continued

```
Pro Pro His Leu Leu Gly Arg Leu Gln Gly Gln Pro Leu Arg Asp Gly
            100                 105                 110

Glu Glu Val Val Leu Leu Glu Gly Ile His Arg Glu Pro Ser His
        115                 120                 125

Ala Gly Pro Leu Asp Phe Ser Cys Asn Ala Gly Lys Ser Cys Pro Arg
130                 135                 140

Ala Asp Val Thr Leu Glu Glu Lys Gly Cys Ala Ser Gln Val Pro Ser
145                 150                 155                 160

His Ser Pro Lys Lys Glu Leu Pro Ala Glu Pro Ser Val Leu Gly
                165                 170                 175

Pro Ser Asp Glu Pro Pro Arg Pro Gln Pro Arg Ala Ala Gln Pro Ala
            180                 185                 190

Glu Pro Gly Gln Trp Arg Leu Pro Ser Ser Lys Gln Pro Leu Ser
        195                 200                 205

Pro Gly Pro Gln Lys Thr Phe Gln Ala Leu Gln Glu Ser Ser Pro Gln
        210                 215                 220

Gly Pro Ser Pro Trp Pro Glu Glu Ser Ser Arg Asp Gln Glu Leu Ala
225                 230                 235                 240

Ala Val Leu Glu Cys Leu Thr Phe Glu Asp Val Pro Glu Asn Lys Ala
                245                 250                 255

Trp Pro Ala His Pro Leu Gly Phe Gly Ser Arg Thr Pro Asp Lys Glu
            260                 265                 270

Glu Phe Lys Gln Glu Glu Pro Lys Gly Ala Ala Trp Pro Thr Pro Ile
        275                 280                 285

Leu Ala Glu Ser Gln Ala Asp Ser Pro Gly Val Pro Gly Glu Pro Cys
        290                 295                 300

Ala Gln Ser Leu Gly Arg Gly Ala Ala Ala Ser Gly Pro Gly Glu Asp
305                 310                 315                 320

Gly Ser Leu Leu Gly Ser Ser Glu Ile Leu Glu Val Lys Val Ala Glu
                325                 330                 335

Gly Val Pro Glu Pro Asn Pro Glu Leu Gln Phe Ile Cys Ala Asp Cys
            340                 345                 350

Gly Val Ser Phe Pro Gln Leu Ser Arg Leu Lys Ala His Gln Leu Arg
        355                 360                 365

Ser His Pro Ala Gly Arg Ser Phe Leu Cys Leu Cys Cys Gly Lys Ser
        370                 375                 380

Phe Gly Arg Ser Ser Ile Leu Lys Leu His Met Arg Thr His Thr Asp
385                 390                 395                 400

Glu Arg Pro His Ala Cys His Leu Cys Gly His Arg Phe Arg Gln Ser
                405                 410                 415

Ser His Leu Ser Lys His Leu Leu Thr His Ser Ser Glu Pro Ala Phe
            420                 425                 430

Leu Cys Ala Glu Cys Gly Arg Gly Phe Gln Arg Arg Ala Ser Leu Val
        435                 440                 445

Gln His Leu Leu Ala His Ala Gln Asp Gln Lys Pro Pro Cys Ala Pro
        450                 455                 460

Glu Ser Lys Ala Glu Ala Pro Pro Leu Thr Asp Val Leu Cys Ser His
465                 470                 475                 480

Cys Gly Gln Ser Phe Gln Arg Arg Ser Leu Lys Arg His Leu Arg
                485                 490                 495

Ile His Ala Arg Asp Lys Asp Arg Arg Ser Ser Glu Gly Ser Gly Ser
            500                 505                 510

Arg Arg Arg Asp Ser Asp Arg Arg Pro Phe Val Cys Ser Asp Cys Gly
        515                 520                 525
```

```
Lys Ala Phe Arg Arg Ser Glu His Leu Trp Ala His Arg Arg Val His
    530                 535                 540

Thr Gly Glu Arg Pro Phe Ser Cys Gln Ala Cys Gly Arg Ser Phe Thr
545                 550                 555                 560

Gln Ser Ser Gln Leu Val Ser His Gln Arg Val His Thr Gly Glu Lys
                565                 570                 575

Pro Tyr Ala Cys Pro Gln Cys Gly Lys Arg Phe Val Arg Arg Ala Ser
            580                 585                 590

Leu Ala Arg His Leu Leu Thr His Gly Gly Pro Arg Pro His His Cys
        595                 600                 605

Thr Gln Cys Gly Lys Ser Phe Gly Gln Thr Gln Asp Leu Ala Arg His
    610                 615                 620

Gln Arg Ser His Thr Gly Glu Lys Pro Cys Arg Cys Ser Glu Cys Gly
625                 630                 635                 640

Glu Gly Phe Ser Gln Ser Ala His Leu Ala Arg His Gln Arg Ile His
                645                 650                 655

Thr Gly Glu Lys Pro His Ala Cys Asp Thr Cys Gly His Arg Phe Arg
            660                 665                 670

Asn Ser Ser Asn Leu Ala Arg His Arg Arg Ser His Thr Gly Glu Arg
        675                 680                 685

Pro Tyr Ser Cys Gln Thr Cys Gly Arg Ser Phe Arg Arg Asn Ala His
    690                 695                 700

Leu Arg Arg His Leu Ala Thr His Ala Glu Pro Gly Gln Glu Gln Ala
705                 710                 715                 720

Glu Pro Pro Gln Glu Cys Val Glu Cys Gly Lys Ser Phe Ser Arg Ser
                725                 730                 735

Cys Asn Leu Leu Arg His Leu Leu Val His Thr Gly Ala Arg Pro Tyr
            740                 745                 750

Ser Cys Thr Gln Cys Gly Arg Ser Phe Ser Arg Asn Ser His Leu Leu
        755                 760                 765

Arg His Leu Arg Thr His Ala Arg Glu Thr Leu Tyr
    770                 775                 780

<210> SEQ ID NO 34
<211> LENGTH: 2568
<212> TYPE: DNA
<213> ORGANISM: Homo sapiens

<400> SEQUENCE: 34
atgcttggag aatcagtccc agctgccctg gagcaggagc agctggggga agtcaagctg      60
gaggaggagg aggctgtcag cccagaggac cccaggcgac cagagtccag gctgaggccc     120
gaggtggctc accagctgtt cagatgcttc cagtatcagg aggacatggg gccacgggcg     180
tccctgagcc ggctccggga gctctgcggc cactggctgc ggccggctct gcacaccaag     240
aaacagatcc tggagctgct ggtgctggag cagttcctga gtgtgctgcc tcgcacctc      300 ctgggccgcc tgcaggggca gccgctcagg gatgggagg aggtggtgct gctgctcgag      360
ggcatccacc gggagcccag ccacgcgggg ccgctggtga gagggtgggg cagcgggctg      420
agcagcatgc ggatgatggg gacttgatcc ccccagtgag gaatctctgg aaactccact      480
ttcccccacc tgaccattcc ttcttcacct cctaactcct ccctggctg actctaacct      540 cgtttctgtc ccatgtcccc tcggagtcag gacacaggtt gccacccgg gagtcactta      600 acttgaatgt gttttgaaca ggattttagt tgtaatgctg caagagttg ccccgtgca       660 gacgtcacct tggaggaaaa ggggtgtgct tcccaggtcc ccagccacag ccccaagaag     720
```

```
gaattgcctg cggaagagcc ttcagtgctg ggcccatcgg atgagcctcc ccgaccccag      780
ccaagggctg cccagcctgc tgagccggga cagtggaggc ttcccccaag ttcaaagcag      840
ccgctgagcc cggggcccca agacattc caggccctgc aagaaagcag tccccagggc        900
ccctcaccat ggccagagga gagttcccga gatcaggagc tggcggctgt gctggagtgc      960
ctgacctttg aggatgtgcc agagaataag gcgtggcctg cacacccct gggattcgga     1020 agcagaaccc cagacaagga ggaatttaaa caagaagagc ccaaggggc tgcctggccc      1080 actcccatct tagcagagtc ccaggcagat agtcctgggg tgccgggaga gccttgcgcc     1140
cagtcgctcg gacgggcgc tgcggctagc ggccctggcg aagatgggtc ccttcttggc      1200
agcagtgaaa ttttggaggt caaagtggct gagggcgtcc ccgagcccaa tccggagttg     1260
cagttcatct gcgcggactg cggggtgagc ttcccgcagc tgtctcgcct gaaggcgcac     1320
cagctgcgct cgcacccggc tgggcgctcc ttcctgtgcc tttgctgcgg aagagcttc      1380 ggccgcagct ccattctcaa gctgcacatg cgcactcaca cggacgagcg gccgcacgcc     1440
tgccacctgt gcggccaccg cttccgccag agctcgcacc tgagcaagca cctgctgacc     1500
cactcctccg aacccgcctt cctgtgcgca gagtgcggcc gcggcttcca cgccgcgcc      1560 agccttgtgc agcacctgct ggcgcacgcc caggaccaga agccgccctg cgctcctgag     1620
agtaaggccg aagcgccgcc actgaccgat gtcctgtgct cccactgcgg ccagagcttc     1680
cagcgccgct ccagcctcaa gcgccacctg cggatccacg ccaggacaa ggaccgccgg      1740 tcctccgaag gctccggcag ccgccgccgg gactccgacc ggaggccctt cgtgtgcagc     1800
gactgcggca aggccttccg gcgcagcgag cacctggtgg cccaccggag ggtgcacacg     1860
ggcgagcggc ccttctcctg ccaggcttgc ggccgcagct tcacgcagag ctcgcagctg     1920
gtcagccacc aacgggtgca cacgggcgag aagccctacg cctgtccgca gtgcgggaag     1980
cgctttgtgc gccgggccag ccttgcccgc cacctgctga cccacggtgg ccctcggccc     2040
caccactgca cccagtgcgg gaagagtttc ggccagaccc aggatctggc ccgccaccag     2100
cgcagccaca cgggcgagaa gccctgccgc tgcagcgagt gcggtgaggg cttcagccag     2160
agcgcccacc tggcgcgcca ccagcgcatc cacacagggg agaagcccca cgcctgcgac     2220
acctgcggcc accgtttccg caatagctcc aacctggccc ccatcgccg cagccacacg     2280 ggcgagcggc cctacagctg tcagacgtgc ggtcgcagct ccggcgcaa cgcgcatctg     2340 cggcggcacc tggctaccca tgcggagccc gggcaggagc aggccgagcc ccgcaggag     2400 tgcgtggagt gcgggaagag cttcagccgc agctgcaatc tgctgcgaca cctgctggtg     2460
cacacgggcg ccaggcccta ctcctgcacg cagtgtggcc gcagcttcag ccgcaactcc     2520
cacctgctgc gccacctgcg cacccacgcc cgcgagacgc tgtactag                  2568
```

<210> SEQ ID NO 35
<211> LENGTH: 2343
<212> TYPE: DNA
<213> ORGANISM: Homo sapiens

<400> SEQUENCE: 35

```
atgcttggag aatcagtccc agctgccctg gagcaggagc agctggggga agtcaagctg       60
gaggaggagg aggctgtcag cccagaggac cccaggcgac cagagtccag gctgaggccc      120
gaggtggctc accagctgtt cagatgcttc cagtatcagg aggacatggg gccacgggcg      180
tccctgagcc ggctccggga gctctgcggc cactggctgc ggccggctct gcacaccaag      240
aaacagatcc tggagctgct ggtgctggag cagttcctga gtgtgctgcc tccgcacctc      300
```

```
ctgggccgcc tgcaggggca gccgctcagg gatgggagg aggtggtgct gctgctcgag      360
ggcatccacc gggagcccag ccacgcgggg ccgctggatt ttagttgtaa tgctggcaag      420
agttgtcccc gtgcagacgt caccttggag gaaaaggggt gtgcttccca ggtccccagc      480
cacagcccca agaaggaatt gcctgcggaa gagccttcag tgctgggccc atcggatgag      540
cctccccgac cccagccaag ggctgccag cctgctgagc cgggacagtg gaggcttccc       600
ccaagttcaa agcagccgct gagcccgggg ccccagaaga cattccaggc cctgcaagaa      660
agcagtcccc agggccctc accatggcca gaggagagtt cccgagatca ggagctggcg       720
gctgtgctgg agtgcctgac ctttgaggat gtgccagaga ataaggcgtg gcctgcacac      780
cccctgggat tcggaagcag aaccccagac aaggaggaat ttaaacaaga gagcccaaa      840
ggggctgcct ggcccactcc catcttagca gagtcccagg cagatagtcc tggggtgccg      900
ggagagcctt gcgcccagtc gctcggacgg ggcgctgcgg ctagcggccc tggcgaagat      960
gggtccttc ttggcagcag tgaaattttg gaggtcaaag tggctgaggg cgtccccgag      1020
cccaatccgg agttgcagtt catctgcgcg gactgcgggg tgagcttccc gcagctgtct      1080
cgcctgaagg cgcaccagct gcgctcgcac ccggctgggc gctccttcct gtgcctttgc      1140
tgcgggaaga gcttcggccg cagctccatt ctcaagctgc acatgcgcac tcacacggac      1200
gagcggccgc acgcctgcca cctgtgcggc caccgcttcc gccagagctc gcacctgagc      1260
aagcacctgc tgacccactc ctccgaaccc gccttcctgt gcgcagagtg cggccgcggc      1320
ttccagcgcc gcgccagcct tgtgcagcac tgctggcgc acgcccagga ccagaagccg      1380
ccctgcgctc ctgagagtaa ggccgaagcg ccgccactga ccgatgtcct gtgctcccac      1440
tgcggccaga gcttccagcg ccgctccagc ctcaagcgcc acctgcggat ccacgccagg      1500
gacaaggacc gccggtcctc cgaaggctcc ggcagccgcc gcgggactc cgaccggagg      1560
cccttcgtgt gcagcgactg cggcaaggcc ttccggcgca gcgagcacct ggtggcccac      1620
cggagggtgc acacgggcga gcggccctt cctgccagg cttgcggccg cagcttcacg       1680
cagagctcgc agctggtcag ccaccaacgg gtgcacacgg gcgagaagcc ctacgcctgt      1740
ccgcagtgcg ggaagcgctt tgtgcgccgg gccagccttg cccgccacct gctgacccac      1800
ggtggccctc ggccccacca ctgcacccag tgcgggaaga gtttcggcca gacccaggat      1860
ctggcccgcc accagcgcag ccacacgggc gagaagccct gccgctgcag cgagtgcggt      1920
gagggcttca gccagagcgc ccacctggcg cgccaccagc gcatccacac aggggagaag      1980
ccccacgcct gcgacacctg cggccaccgt ttccgcaata gctccaacct ggcccgccat      2040
cgccgcagcc acgggcga gcggccctac agctgtcaga cgtgcggtcg cagcttccgg       2100
cgcaacgcgc atctgcggcg gcacctggct acccatgcgg agcccgggca ggagcaggcc      2160
gagccccgc aggagtgcgt ggagtgcggg aagagcttca gccgcagctg caatctgctg      2220
cgacacctgc tggtgcacac gggcgccagg ccctactcct gcacgcagtg tggccgcagc      2280
ttcagccgca actcccacct gctgcgccac ctgcgcaccc acgcccgcga gacgctgtac      2340
tag                                                                   2343

<210> SEQ ID NO 36
<211> LENGTH: 2175
<212> TYPE: DNA
<213> ORGANISM: Homo sapiens

<400> SEQUENCE: 36
atgcttggag aatcagtccc agctgccctg gagcaggagc agctggggga agtcaagctg      60
```

```
gaggaggagg aggctgtcag cccagaggac cccaggcgac cagagtccag gctgaggccc      120
gaggtggctc accagctgtt cagatgcttc cagtatcagg aggacatggg gccacgggcg      180
tccctgagcc ggctccggga gctctgcggc cactggctgc ggccggctct gcacaccaag      240
aaacagatcc tggagctgct ggtgctggag cagttcctga gtgtgctgcc tccgcacctc      300
ctgggccgcc tgcaggggca gccgctcagg gatggggagg aggtggtgct gctgctcgag      360
ggcatccacc gggagcccag ccacgcgggg ccgctggatt ttagttgtaa tgctggcaag      420
agttgtcccc gtgcagacgt caccttggag gaaaaggggt gtgcttccca ggtccccagc      480
cacagcccca agaaggaatt gcctgcggaa gagccttcag tgctgggccc atcggatgag      540
cctccccgac cccagccaag ggctgccag cctgctgagc cgggacagtg gaggcttccc       600
ccaagttcaa agcagccgct gagccgggg ccccagaaga cattccaggc cctgcaagaa       660
agcagtcccc agggccctc accatggcca aggagagtt cccgagatca ggagctggcg       720
gctgtgctgg agtgcctgac cttgaggat gtgccagaga ataaggcgtg gcctgcacac       780
cccctgggat tcggaagcag aaccccagac aaggaggaat ttaaacaaga gagcccaaa      840 ggggctgcct ggcccactcc catcttagca gagtcccagg cagatagtcc tggggtgccg      900
ggagagcctt gcgcccagtc gctcggacgg ggcgctgcgg ctagcggccc tggtgaagat      960 gggtccctc ttggcagcag tgaaattttg gaggtcaaag tggctgaggg cgtccccgag     1020
cccaatccgg agttgcagtt catctgcgcg gactgcgggg tgagcttccc gcagctgtct     1080
cgcctgaagg cgcaccagct gcgctcgcac ccggctgggc gctccttcct gtgcctttgc     1140
tgcgggaaga gcttcggccg cagctccatt ctcaagctgc acatgcgcac tcacacggac     1200
gagcggccgc acgcctgcca cctgtgcggc accgcttcc gccagagctc gcacctgagc      1260
aagcacctgc tgacccactc ctccgaaccc gccttcctgt gcgcagagtg cggccgcggc     1320
ttccagcgcc gcgccagcct tgtgcagcac ctgctggcgc acgcccagga ccagaagccg     1380
ccctgcgctc ctgagagtaa ggccgaagcg ccgccactga ccgatgtcct gtgctcccac     1440
tgcggccaga gcttccagcg ccgctccagc ctcaagcgcc acctgcggat ccacgccagg     1500
gacaaggacc gccggtcctc cgaaggctcc ggcagccgcc gcgggactc cgaccggagg      1560 cccttcgtgt gcagcgactg cggcaaggcc ttccggcgca gcgagcacct ggtgcccac      1620 cggagggtgc acacgggcga gcggcccttc tcctgccagg cttgcggccg cagcttcacg     1680
cagagctcgc agctggtcag ccaccaacgg gtgcacacgg gcgagaagcc ctacgcctgt     1740
ccgcagtgcg ggaagcgctt tgtgcgccgg gccagccttg cccgccacct gctgacccac     1800
ggtggccctc ggccccacca ctgcacccag tgcgggaaga gtttcggcca gacccaggat     1860
ctggctcgcc accagcgcag ccacacgggc gagcggccct acagctgtca gacgtgcggt     1920
cgcagcttcc ggcgcaacgc gcatctgcgg cggcacctgg ctaccatgc ggagcccggg     1980 caggagcagg ccgagccccc gcaggagtgc gtggggtgcg ggaagagctt cagccgcagc     2040
tgcaatctgc tgcgacacct gctggtgcac acgggcgcca ggcctactc ctgcacgcag     2100 tgtggccgca gcttcagccg caactcccac ctgctgcgcc acctgcgcac ccacgcccgc     2160
gagacgctgt actag                                                     2175
```

<210> SEQ ID NO 37
<211> LENGTH: 2075
<212> TYPE: DNA
<213> ORGANISM: Homo sapiens

<400> SEQUENCE: 37

-continued

```
atgcttggag aatcagtccc agctgccctg gagcaggagc agctggggga agtcaagctg    60
gaggaggagg aggctgtcag cccagaggac cccaggcgac cagagtccag gctgaggccc   120
gaggtggctc accagctgtt cagatgcttc cagtatcagg aggacatggg ccacgggcg    180 tccctgagcc ggctccggga gctctgcggc cactggctgc ggccggctct gcacaccaag   240
aaacagatcc tggagctgct ggtgctggag cagttcctga gtgtgctgcc tccgcacctc   300
ctgggccgcc tgcaggggca gccgctcagg gatgggagg aggtggtgct gctgctcgag    360
ggcatccacc gggagcccag ccacgcgggg ccgctggtcc caggccccc tcaccatggc    420 cagaggagag ttcccgagat caggagctgg cggctgtgct ggagtgcctg acctttgagg   480
atgtgccaga gaataaggcg tggcctgcac acccctggg attcggaagc agaaccccag    540
acaaggagga atttaaacaa gaagagccca aggggctgc ctggcccact ccatcttag     600 cagagtccca ggcagatagt cctggggtgc cgggagagcc ttgcgcccag tcgctcggac   660
ggggcgctgc ggctagcggc cctggcgaag atgggtccct tcttggcagc agtgaaattt   720
tggaggtcaa agtggctgag ggcgtccccg agcccaatcc ggagttgcag ttcatctgcg   780
cggactgcgg ggtgagcttc ccgcagctgt ctcgcctgaa ggcgcaccag ctgcgctcgc   840
acccggctgg gcgctccttc ctgtgccttt gctgcgggaa gagcttcggc cgcagctcca   900
ttctcaagct gcacatgcgc actcacacgg acgagcggcc gcacgcctgc cacctgtgcg   960
gccaccgctt ccgccagagc tcgcacctga gcaagcacct gctgacccac tcctccgaac  1020
ccgccttcct gtgcgcagag tgcggccgcg gcttccagcg ccgcgccagc cttgtgcagc  1080
acctgctggc gcacgcccag gaccagaagc cgccctgcgc tcctgagagt aaggccgaag  1140
cgccgccact gaccgatgtc ctgtgctccc actgcggcca gagcttccag cgccgctcca  1200
gcctcaagcg ccacctgcgg atccacgcca gggacaagga ccgccggtcc tccgaaggct  1260
ccggcagccg ccgccgggac tccgaccgga ggcccttcgt gtgcagcgac tgcggcaagg  1320
ccttccggcg cagcgagcac ctggtggccc accggagggt gcacacgggc gagcggccct  1380
tctcctgcca ggcttgcggc cgcagcttca cgcagagctc gcagctggtc agccaccaac  1440
gggtgcacac gggcgagaag ccctacgcct gtccgcagtg cgggaagcgc tttgtgcgcc  1500 gggcagcct tgcccgccac ctgctgaccc acggtggccc tcggcccac cactgcaccc   1560 agtgcgggaa gagtttcggc cagacccagg atctggcccg ccaccagcgc agccacacgg  1620
gcgagaagcc ctgccgctgc agcgagtgcg gtgagggctt cagccagagc gcccacctgg  1680
cgcgccacca gcgcatccac acaggggaga agcccacgc ctgcgacacc tgcggccacc   1740
gtttccgcaa tagctccaac ctggcccgcc atcgccgcag ccacgggc gagcggccct     1800 acagctgtca gacgtgcggt cgcagcttcc ggcgcaacgc gcatctgcgg cggcacctgg  1860
ctacccatgc ggagcccggg caggagcagg ccgagccccc gcaggagtgc gtggagtgcg  1920
ggaagagctt cagccgcagc tgcaatctgc tgcgacacct gctggtgcac acgggcgcca  1980
ggccctactc ctgcacgcag tgtggccgca gcttcagccg caactccac ctgctgcgcc   2040 acctgcgcac ccacgcccgc gagacgctgt actag                              2075
```

ZNF206: REGULATOR OF EMBRYONIC STEM CELL SELF-RENEWAL AND PLURIPOTENCY

TECHNICAL FIELD

The present invention relates to stem cell research, particularly to genes involved in regulation of self-renewal and pluripotency of stem cells, such as, for example, human embryonic stem cells.

BACKGROUND INFORMATION

Several transcriptional factors have been implicated in human embryonic stem cell (hESC) self-renewal supporting a view that this process is regulated at the level of transcriptional control (Chambers, Cloning Stem Cells 6:386-391, 2004).

The transcription factor POU5F1 (OCT4) is essential for embryonic stem cell (ESC) pluripotency and appears to regulate a number of ESC properties. OCT4 is specifically expressed in ESCs, pre-implantation embryos, epiblast, and germ cells (Okamoto et al., Cell 60:461-472, 1990; Scholer et al., EMBO J. 9:2185-2195, 1990). Inactivation of OCT4 in mouse embryos and ESCs results in loss of pluripotency and spontaneous differentiation into the trophoblast lineage (Niwa et al., Nat. Genet. 24:372-376, 2000). Mouse ESCs (mESCs), even when constitutively expressing OCT4 from an exogenous promoter, still require LIF for self-renewal suggesting that LIF and OCT4 function in different pathways. However, overexpression of OCT4 induces mESCs to differentiate into PE (Niwa et al., Nat. Genet. 24:372-376, 2000).

The homeodomain-containing transcription factor NANOG is another critical ESC factor recently identified (Chambers et al., Cell 113:643-655, 2003; Mitsui et al., Cell 113:631-642, 2003). The NANOG-deficient ICM fails to generate an epiblast and only produces extraembryonic primitive endoderm (PE). Similarly in culture, NANOG-deficient ESCs lose pluripotency and differentiate to a PE lineage. Unlike POU5F1/OCT4, NANOG overexpression can maintain ESC self-renewal without LIF (Chambers et al., Cell 113:643-655, 2003). It has been proposed that NANOG maintains ESC self-renewal through repression of genes that promote differentiation, e.g., GATA4 and GATA6, which are upregulated in NANOG-deficient cells. That NANOG also binds sequences in the GATA6 gene supports this hypothesis (Mitsui et al., Cell 113:631-642, 2003).

Together, these observations suggest that NANOG is a critical factor underlying pluripotency in both ICM and ESCs by repressing their differentiation into PE, and that NANOG and OCT4 work together in the maintenance of the undifferentiated state by virtue of overlapping functions. Two cell fate decisions have to be made during pre-implantation development. The first is that cells of the morula remain pluripotent or differentiate into trophectoderm. The second is that cells of the ICM remain pluripotent as epiblast or differentiate into PE. OCT4 is the key determinant of the first decision (since OCT4-null ESCs differentiate into trophectoderm), while NANOG is the crucial determinant of the second decision (since ESCs lacking NANOG differentiate into PE) (Mitsui et al., Cell 113:631-642, 2003). FIG. 1 shows transcription factors involved in controlling self-renewal of human embryonic stem cells by repressing early lineage commitment.

Two other transcription factors have been identified that interact with OCT4: the forkhead transcription factor FOXD3 and the Sry-related factor SOX2. FOXD3 is expressed in the blastocyst and later in the post-implantation egg cylinder epiblast. FOXD3 physically interacts with OCT4 to activate the ostopontin enhancer, which is expressed in ESCs (Guo et al., Proc. Natl. Acad. Sci. U.S.A. 99:3663-3667, 2002). Sox2 is expressed in ESCs as well as in multipotent embryonic and extra-embryonic lineages. Disrupting Sox2 results in pre-implantation embryonic lethality (Avilion et al., Genes Dev. 17:126-140, 2003). Sox2 was identified as a co-factor of OCT4 for activating FGF4, which is restrictively expressed in undifferentiated ESCs, and is essential for post-implantation mouse development and limb patterning and growth (Yuan et al., Genes Dev. 9:2635-2645, 1995). Transcriptional regulation of NANOG itself is also regulated by OCT4 and SOX2 (Rodda et al., J. Biol. Chem. 280: 24731-24737, 2005). Another OCT4 and SOX2 co-regulated gene is the ESC-specific transcription factor UTF1 (Nishimoto et al., Mol. Cell. Biol. 19:5453-5465, 1999). Taken together, these studies suggest that the SOX2-OCT4 complex is at the apex of a regulatory hierarchy of the "pluripotency genetic regulatory network".

FIG. 1 shows transcription factors involved in controlling self-renewal by repressing early lineage commitment.

In summary, ESC identity is determined by cell-intrinsic transcription factors that need to be expressed at particular levels in order to function appropriately. However, the molecular basis of the regulation of pluripotency and early lineage commitment of hESCs is still poorly understood. Additional intrinsic pathway-specific transcription factors presumably exist that maintain expression of the thousands of genes that are expressed in ESCs and control different types of renewal and differentiation pathways. Understanding how hESCs maintain their pluripotency and self-renewal and execute precise differentiation programs will require extending our understanding of the transcriptional regulatory hierarchy of hESC function, including identifying new intrinsic transcription factors.

SUMMARY OF THE INVENTION

We have identified zinc finger protein 206 (ZNF206), a novel repressor of human embryonic stem cell (hESC) differentiation. Repressing extra-embryonic endoderm development preserves the pluripotent state of human embryonic stem cells, and, conversely downregulating expression of ZNF206 in hESCs causes them to upregulate the expression of genes associated with the extra-embryonic endodermal lineage, down-regulate genes associated with the pluripotent state, and may lead to the further emergence of genes associated with even more differentiated lineages and phenotypes.

According to one aspect of the invention, isolated polynucleotides are provided that comprise a sequence that has at least 90%, or 95%, or 100% nucleic acid sequence identity to a native ZNF206 polynucleotide and that hybridize selectively to the native ZNF206 polynucleotide. The isolated polynucleotide of claim 1 wherein the sequence that has at least 95% identity to a native ZNF206 polynucleotide. According to another embodiment, such isolated polynucleotides comprise a sequence at least 100 nucleotides in length that has at least 90%, 95%, or 99% nucleic acid sequence identity to a native ZNF206 polynucleotide.

According to another embodiment of the invention, isolated polynucleotides are provided that comprise at least 15, 20, or 30 contiguous nucleotides of a native ZNF206 polynucleotide, wherein the isolated polynucleotide hybridizes selectively to a native ZNF206 polynucleotide. According to one embodiment, the isolated polynucleotide comprises a full-length protein-coding sequence of a native ZNF206 mRNA or cDNA. According to another embodiment, the isolated polynucleotide encodes a polypeptide that has ZNF206 activity.

According to another embodiment of the invention, cells are provided that comprise any of the isolated polynucleotides described above. According to another embodiment, cells, vectors (including, but not limited to expression vectors), probes and primers are provided that comprise any of the isolated polynucleotides described above. Also provided are cells that comprise such vectors.

According to another embodiment of the invention, kits are provided that comprise: (a) a first primer comprising at least 15 contiguous nucleotides of a native ZNF206 polynucleotide, wherein the first primer hybridizes selectively to a native ZNF206 polynucleotide; (b) a second primer comprising at least 15 contiguous nucleotides of the native ZNF206 polynucleotide; and (c) suitable packaging enclosing the first primer and the second primer, wherein an amplification reaction performed using the first primer, the second primer, and a sample comprising a ZNF206 mRNA produces an amplification product that indicates the presence of the ZNF206 mRNA in the sample.

According to another embodiment of the invention, isolated polypeptides of at least 11 amino acids are provided that comprise at least 4, 5, 6, 7, 8, 9, or 10 contiguous amino acids of a native ZNF206 polypeptide, and, that when introduced into a mammal, elicits production of an antibody that binds selectively to a native ZNF206 polypeptide. According to another embodiment of the invention, isolated polypeptides are provided that comprise at least 11, 12, 15, 20, or 30 contiguous amino acids of a native ZNF206 polypeptide, and, that when introduced into a mammal, elicits production of an antibody that binds selectively to a native ZNF206 polypeptide, including but not limited to a full-length native ZNG206 polypeptide.

According to another embodiment of the invention, isolated polypeptides are provided that comprise a sequence that has at least 90%, 91, 92, 93, 94, 95%, 96%, 97%, 98%, 99% or 100% amino acid sequence identity to a native ZNF206 polypeptide, wherein introduction of the isolated polypeptide into a mammal elicits production of an antibody that selectively binds to ZNF206. According to another embodiment of the invention, such isolated polypeptides comprise a sequence at least 15, 16, 17, 18, 19, 20, 30, 40 or more amino acids in length that has such a degree of amino acid sequence identity. According to another embodiment of the invention, such isolated polypeptides have ZNF206 activity.

According to another embodiment of the invention, isolated polynucleotides are provided that encode any of the aforementioned polypeptides.

According to another embodiment of the invention, antibodies are provided that bind selectively to a native ZNF206 polypeptide, including, but not limited to, monoclonal, polyclonal, chimeric, humanized, single-chain, and fragment antibodies, for example.

According to another embodiment of the invention, methods are provided for making an antibody that binds selectively to a native ZNF206 polypeptide comprising introducing into a mammal (a) an expression vector comprising one of the aforementioned polynucleotides, or (b) one of the aforementioned isolated polypeptides, thereby eliciting production of the antibody.

According to another embodiment of the invention, pharmaceutical compositions are provided that comprise (a) a vector comprising a promoter suitable for expression in the cell operably linked to an isolated polynucleotide comprising a sequence that has at least 90% nucleic acid sequence identity to a native ZNF206 polynucleotide and that hybridizes selectively to the native ZNF206 polypeptide, wherein expression of the polynucleotide in the cell causes a reduction in ZNF206 polypeptide levels in the cell, and (b) a pharmaceutically acceptable carrier.

According to another embodiment of the invention, methods are provided for making a medicament for treating a patient with a cancer or at risk for developing the cancer, the method comprising formulating the medicament with a pharmaceutically effective amount of a vector comprising a promoter suitable for expression in the cell operably linked to an isolated polynucleotide comprising a sequence that has at least 90% nucleic acid sequence identity to a native ZNF206 polynucleotide and that hybridizes selectively to the native ZNF206 polypeptide, wherein expression of the polynucleotide in the cell causes a reduction in ZNF206 polypeptide levels in the cell.

According to another embodiment of the invention, methods are provided for detecting the presence of a ZNF206 polynucleotide in a sample comprising the ZNF206 polynucleotide, the method comprising contacting the sample with a probe or primer comprising a polynucleotide sequence that binds selectively to the ZNF206 polynucleotide and detecting binding of the probe or primer to the ZNF206 mRNA. One such embodiment, comprises (a) contacting the sample with a first primer that comprises the polynucleotide sequence that hybridizes selectively to the ZNF206 mRNA and a second primer comprising a polynucleotide sequence that hybridizes to the ZNF206 mRNA, (b) performing an amplification reaction to produce an amplification product that indicates the presence of the ZNF206 mRNA in the sample, and (c) detecting the amplification product, including, but not limited to, a PCR reaction.

According to another embodiment of the invention, methods are provided for detecting the presence of a ZNF206 polypeptide in a sample comprising the ZNF206 polypeptide, the method comprising (a) contacting the sample with an antibody (including, but not limited to, a monoclonal antibody) that binds selectively to the ZNF206 polypeptide and (b) detecting binding of the antibody to the ZNF206 polypeptide. Such methods may, for example, comprise performing ELISA or bio-barcode assays.

According to another embodiment of the invention, methods are provided for assessing the pluripotency of a cell by various means. According to one such embodiment, such methods comprise (a) measuring ZNF206 polypeptide or polynucleotide levels in a sample comprising the cell, and (b) comparing the ZNF206 polypeptide or polynucleotide levels in the sample to a reference. According to another such embodiment, such methods comprise measuring the ZNF206 polypeptide level in the cell by contacting a sample comprising the cell with an antibody that binds selectively to ZNF206 polypeptide (including but not limited to a monoclonal antibody) and measuring binding of the antibody to ZNF206 polypeptide in the sample, such as, for example, by an ELISA or bio-barcode assay. According to another embodiment, such methods comprise measuring the ZNF206 mRNA level in the cell by contacting a sample comprising the cell with a probe or primer that hybridizes selectively to ZNF206 mRNA and measuring hybridization of the probe or primer to the ZNF206 mRNA in the sample. According to another embodiment, such methods comprise measuring the ZNF206 mRNA level in the cell by (a) contacting the sample comprising the cell with one or more primers that comprise a polynucleotide sequence that hybridizes selectively to the ZNF206 mRNA, (b) performing an amplification reaction (including but not limited to a PCR reaction or bio-barcode assay) to produce an amplification product that indicates the presence of ZNF206 mRNA in the sample, and (c) measuring the amplification product. In any of the foregoing methods for assessing the pluripotency of a cell, the sample may be, for example, a tissue sample.

According to another embodiment of the invention, methods are provided for maintaining or increasing the pluripotency of a cell comprising expressing in the cell a vector comprising (a) a promoter suitable for expression in the cell operably linked to (b) an isolated polynucleotide comprising a sequence at least 100 nucleotides in length that has at least 90% nucleic acid sequence identity to a native ZNF206 polynucleotide, wherein expression of the polynucleotide in the cell produces a polypeptide that reduces or prevents differentiation of the cell.

According to another embodiment of the invention, methods are provided for promoting differentiation of a cell comprising reducing ZNF206 expression of the cell. According to one embodiment, such a method comprises expressing in the cell a vector comprising (a) a promoter suitable for expression in the cell operably linked to (b) an isolated polynucleotide comprising a sequence that has at least 90% nucleic acid sequence identity to a native ZNF206 polynucleotide and that hybridizes selectively to the native ZNF206 polypeptide, wherein expression of the polynucleotide in the cell causes a reduction in ZNF206 polypeptide levels in the cell.

According to another embodiment of the invention, methods are provided for diagnosing a cancer characterized by elevated levels of ZNF206 comprising (a) obtaining a sample comprising a cell, (b) determining ZNF206 polypeptide or polynucleotide levels in the sample, and (c) comparing the ZNF206 polypeptide or polynucleotide levels in the sample with a reference.

According to another embodiment of the invention, methods are provided for treating a cancer characterized by elevated levels of ZNF206 comprising administering to a patient in need of such treatment a composition comprising a vector comprising (a) a promoter suitable for expression in a cell of the patient operably linked to (b) an isolated polynucleotide comprising a sequence at least 100 nucleotides in length that has at least 90% nucleic acid sequence identity to a native ZNF206 polynucleotide, wherein expression of the polynucleotide in the cell reduces ZNF206 polypeptide levels in the cell.

According to another embodiment of the invention, methods are provided for diagnosing a disease state resulting from a mutation in a ZNF206 polynucleotide comprising (a) providing a sample from a patient comprising a cell and (b) determining whether the sample comprises a mutated ZNF206 polynucleotide. The presence of a mutated ZNF 206 polynucleotide in the sample may be determined, for example by: contacting the sample with a polynucleotide probe or primer that hybridizes specifically to a mutated ZNF206 polynucleotide sequence; by contacting the sample with one or more primers that comprise a polynucleotide sequence that hybridizes selectively to the mutated ZNF206 polynucleotide, and performing an amplification reaction (e.g., a PCR or bio-barcode assay) to produce an amplification product that indicates the presence of the mutated ZNF206 polynucleotide in the sample; by detecting a restriction fragment length polymorphism; or by contacting the sample with an antibody probe that hybridizes specifically to a mutated ZNF polypeptide sequence encoded by the mutated ZNF polynucleotide.

Any of the aforementioned methods may be automated.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE FIGURES

FIG. 7 shows the generation of a polyclonal rabbit antibody against the human ZNF206 proteins (SEQ ID NO: 33). Underlined is the peptide (amino acids 711-726) used to immunize rabbits against the human ZNF206 protein. The polyclonal antibody detects a protein that is approximately 80 kD in size in undifferentiated hES cell line H9 and not in the hES-derived PEL differentiated cells.

FIG. 10 shows the DNA sequence for four isoforms of ZNF206 (SEQ ID NOS: 34-37, respectively in order of appearance).

DETAILED DESCRIPTION OF THE INVENTION

Definitions and Methods

Figure 1:
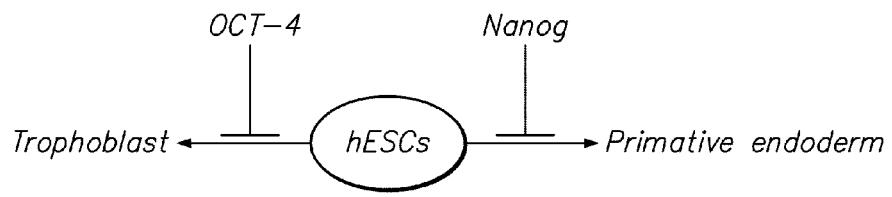
FIG. 1 shows transcription factors involved in controlling self-renewal of human embryonic stem cells by repressing early lineage commitment.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 CFR 1.822 is used. The standard one- and three-letter nomenclature for amino acid residues is used.

Polynucleotides

As used herein, the term "ZNF206 polynucleotide" refers to the ZNF206 genomic DNA, mRNA, and cDNA corresponding to the mRNA as present in humans (including any of the several human isoforms of ZNF206) or non-human species, such as, for example, in the chimpanzee, mouse or chicken (Bernot et al., Genomics 50:147-160, 1998). Also encompassed by the term "ZNF206 polynucleotides" are, for example: fragments or portions of the ZNF206 mRNA or cDNA, including but not limited to, a ZNF206 polynucleotide; fragments that encode antigenic determinants of ZNF206 (e.g., those that elicit antibodies that bind selectively to ZNF206 polypeptide); probes and primers that hybridize selectively to ZNF206 polynucleotides; etc. Also included are mutated or variant polynucleotides that include one or more nucleotide insertions, deletions, or substitutions from the wild-type ZNF206 sequence, but that, for example: retain the ability to bind selectively to ZNF206; encode a polypeptide that includes a ZNF206 antigenic determinant; encode a polypeptide having ZNF206 activity; etc.

As used herein, the term "hybridizes selectively" refers to binding of a probe, primer or other polynucleotide, under stringent hybridization conditions, to a target polynucleotide, such as a native, or wild-type, ZNF206 mRNA or cDNA, to a substantially higher degree than to other polynucleotides. Probes and primers that hybridize selectively to ZNF206 include sequences that are unique to ZNF206. In particular, a probe that "hybridizes selectively" to ZNF206 does not hybridize substantially to ZNF206 under stringent hybridization conditions and therefore can be used to distinguish a ZNF206 polynucleotide (e.g., a ZNF206 mRNA) from a ZNF206 polynucleotide. Similarly, a primer that "hybridizes selectively" to ZNF206, when used in an amplification reaction such as PCR, results in amplification of ZNF206 without resulting in substantial amplification of ZNF206 under suitable amplification conditions. Thus, all or substantially all of a ZNF206-selective probe or primer hybridizes to the target ZNF206 polynucleotide under suitable conditions, as can be determined given the sensitivity of a particular procedure. Similarly, as used herein, the term "selective for" in reference to a polynucleotide, indicates that the polynucleotide hybridizes selectively to a target polynucleotide.

Similarly, a probe or primer that includes a sequence that is unique to ZNF206 hybridizes selectively to ZNF206. In particular, a probe that hybridizes selectively to ZNF206 does not hybridize substantially to ZNF206 under stringent hybridization conditions and therefore can be used to distinguish a ZNF206 polynucleotide (e.g., a ZNF206 mRNA) from a ZNF206 polynucleotide. Similarly, a primer that hybridizes selectively to a ZNF206 polynucleotide, when used in an amplification reaction such as PCR, results in amplification of the ZNF206 polynucleotide without resulting in substantial amplification of ZNF206 polynucleotide. Thus, all or substantially all of a ZNF206-selective probe or primer hybridizes to the target ZNF206 polynucleotide, as can be determined given the sensitivity of a particular procedure.

As used herein, the terms "wild-type" or "native" in reference to a polynucleotide are used interchangeably to refer to a polynucleotide that has 100% sequence identity with a reference polynucleotide that can be found in a cell or organism, or a fragment thereof.

Polynucleotide (e.g., DNA or RNA) sequences may be determined by sequencing a polynucleotide molecule using an automated DNA sequencer. A polynucleotide sequence determined by this automated approach can contain some errors. The actual sequence can be confirmed by resequencing the polynucleotide by automated means or by manual sequencing methods well known in the art.

Unless otherwise indicated, each "nucleotide sequence" set forth herein is presented as a sequence of deoxyribonucleotides (abbreviated A, G, C and T). However, the term "nucleotide sequence" of a DNA molecule as used herein refers to a sequence of deoxyribonucleotides, and for an RNA molecule, the corresponding sequence of ribonucleotides (A, G, C and U) where each thymidine deoxynucleotide (T) in the specified deoxynucleotide sequence in is replaced by the ribonucleotide uridine (U).

By "isolated" polynucleotide is intended a polynucleotide that has been removed from its native environment. For example, recombinant polynucleotides contained in a vector are considered isolated for the purposes of the present invention. Further examples of isolated polynucleotides include recombinant polynucleotides maintained in heterologous host cells or purified (partially or substantially) polynucleotides in solution. Isolated RNA molecules include in vivo or in vitro RNA transcripts of the DNA molecules of the present invention. Isolated polynucleotides according to the present invention further include such molecules produced synthetically.

Polynucleotides can be in the form of RNA, such as mRNA, or in the form of DNA, including, for instance, cDNA and genomic DNA. The DNA can be double-stranded or single-stranded. A single-stranded DNA or RNA can be a coding strand, also known as the sense strand, or it can be a non-coding strand, also referred to as the anti-sense strand. Polynucleotides can include non-naturally occurring nucleotide or ribonucleotide analogs.

The term "fragment" (of a polynucleotide) as used herein refers to polynucleotides that are part of a longer polynucleotide having a length of at least about 15, 20, 25, 30, 35, or 40 nucleotides (nt) in length, which are useful, for example, as probes and primers. Thus, for example, a fragment of ZNF206 at least 20 nucleotides in length includes 20 or more contiguous nucleotides from the nucleotide sequence of the ZNF206 full-length cDNA. Such DNA fragments may be generated by the use of automated DNA synthesizers or by restriction endonuclease cleavage or shearing (e.g., by sonication) a full-length ZNF206 cDNA, for example.

Also encompassed by the present invention are isolated polynucleotides that hybridize under stringent hybridization conditions to a ZNF206 polynucleotide such as, for example, a ZNF206 transcript (i.e., mRNA). By "stringent hybridization conditions" is intended overnight incubation at 42° C. in a solution comprising: 50% formamide, 5×SSC (750 mM NaCl, 75 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. Alternatively, stringent hybridizations are conditions used for performance of a polymerase chain reaction (PCR). Such hybridizing polynucleotides are useful diagnostically as a probe according to conventional DNA hybridization techniques or as primers for amplification of a target sequence by the polymerase chain reaction (PCR).

As used herein, the term "hybridizes (or binds) specifically" is used interchangeably with the term "hybridizes (or binds) selectively" means that most or substantially all hybridization of a probe or primer is to a particular polynucleotide in a sample under stringent hybridization conditions.

The present invention also provides polynucleotides that encode all or a portion of a polypeptide, e.g., a full-length ZNF206 polypeptide or a portion thereof. Such protein-coding polynucleotides may include, but are not limited to, those sequences that encode the amino acid sequence of the particular polypeptide or fragment thereof and may also include together with additional, non-coding sequences, including for example, but not limited to introns and non-coding 5' and 3' sequences, such as the transcribed, non-translated sequences that play a role in transcription, mRNA processing—including splicing and polyadenylation signals, e.g., ribosome binding and stability of mRNA; an additional coding sequence which codes for additional amino acids, such as those which provide additional functionalities. In addition, the sequence encoding the polypeptide can be fused to a heterogeneous polypeptide or peptide sequence, such as, for example a marker sequence that facilitates purification of the fused polypeptide. One example of such a marker sequence is a hexa-histidine peptide, such as the tag provided in a pQE vector (Qiagen, Inc.). As described in Gentz et al., Proc. Natl. Acad. Sci. USA 86:821-824 (1989), for instance, hexa-histidine provides for convenient purification of the fusion protein. The "HA" tag is another peptide useful for purification which corresponds to an epitope derived from the influenza hemagglutinin (HA) protein (Wilson et al., Cell 37:767, 1984).

The present invention further relates to variants of the native, or wild-type, polynucleotides of the present invention, which encode portions, analogs or derivatives of a ZNF206 polypeptide. Variants can occur naturally, such as a natural allelic variant, i.e., one of several alternate forms of a gene occupying a given locus on a chromosome of an organism. Non-naturally occurring variants can be produced, e.g., using known mutagenesis techniques or by DNA synthesis. Such variants include those produced by nucleotide substitutions, deletions or additions. The substitutions, deletions or additions can involve one or more nucleotides. The variants can be altered in coding or non-coding regions or both. Alterations in the coding regions can produce conservative or non-conservative amino acid substitutions, deletions or additions. Also included are silent substitutions, additions and deletions, which do not alter the properties and activities of the ZNF206 polypeptide or portions thereof.

Further embodiments of the invention include isolated polynucleotide molecules have, or comprise a sequence having, a high degree of sequence identity with a native, or wild type, ZNF206 polynucleotide, for example, at least 90%, 95%, 96%, 97%, 98% or 99% identical thereto.

A polynucleotide is considered to have a nucleotide sequence at least, for example, 95% "identical" to a reference nucleotide sequence if it is identical to the reference sequence except that it includes up to five mutations (additions, deletions, or substitutions) per each 100 nucleotides of the reference nucleotide sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence. Nucleotide sequence identity may be determined conventionally using known computer programs such as the BESTFIT program (Wisconsin Sequence Analysis Package, Version 8 for Unix, Genetics Computer Group, University Research Park, 575 Science Drive, Madison, Wis. 53711. BESTFIT uses the local homology algorithm of Smith and Waterman, Adv. Appl. Math. 2:482-489 (1981), to find the best segment of homology between two sequences. When using BESTFIT or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Recombinant Constructs: Vectors and Host Cells

The present invention also provides recombinant polynucleotide constructs that comprise a ZNF206 polynucleotide, including but not limited to vectors. The present invention also provides host cells comprising such vectors and the production of ZNF206 polypeptides or fragments thereof by recombinant or synthetic techniques.

"Operably Linked". A first nucleic-acid sequence is "operably linked" with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous, and where necessary to join two protein coding regions, in reading frame.

"Recombinant". A "recombinant" polynucleotide is made by an artificial combination of two otherwise separated segments of sequence, e.g., by chemical synthesis or by the manipulation of isolated segments of polynucleotides by genetic engineering techniques. Techniques for nucleic-acid manipulation are well-known (see, e.g., Sambrook et al., 1989, and Ausubel et al., 1992). Methods for chemical synthesis of polynucleotides are discussed, for example, in Beaucage and Carruthers, Tetra. Letts. 22:1859-1862, 1981, and Matteucci et al., J. Am. Chem. Soc. 103:3185, 1981. Chemical synthesis of polynucleotides can be performed, for example, on commercial automated oligonucleotide synthesizers.

Recombinant vectors are produced by standard recombinant techniques and may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

Expression vectors include sequences that permit expression of a polypeptide encoded by a polynucleotide of interest in a suitable host cell. Such expression may be constitutive or non-constitutive, e.g., inducible by an environmental factor or a chemical inducer that is specific to a particular cell or tissue type, for example. Expression vectors include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

In expression vectors, a polynucleotide insert is operably linked to an appropriate promoter. The promoter may be a homologous promoter, i.e., a promoter or functional portion thereof, that is associated with the polynucleotide insert in nature, for example, a ZNF206 promoter with a ZNF206 or ZNF206 protein coding region. Alternatively, the promoter may be a heterologous promoter, i.e., a promoter or functional portion thereof, that is not associated with the polynucleotide insert in nature, for example, a bacterial promoter used for high-level protein expression in bacterial cells (or, for that matter, any promoter other than a ZNF206 promoter) operably linked to a ZNF206 protein coding region. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vectors may include one or more selectable marker suitable for selection of a host cell into which such a vector has been introduced. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *E. coli, Streptomyces* and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Bacterial promoters suitable include the *E. coli* lacI and lacZ promoters, the T3 and T7 promoters, the gpt promoter, the lambda PR and PL promoters and the trp promoter. Eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

A polypeptide of interest may be expressed in a modified form, such as a fusion protein, and may include not only secretion signals but also additional heterologous functional regions. For instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

An expressed polypeptide of interest can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polynucleotide constructs can also be used to reduce expression of ZNF206 in a cell. For example, antisense constructs, ribozymes, short interfering RNA (siRNA) or small hairpin RNA (shRNA), and other such constructs can be used for this purpose.

A "small interfering RNA" or "short interfering RNA" (siRNA) or "short hairpin RNA" (shRNA) is a double-stranded RNA molecule that is complementary to a target nucleic acid sequence, for example, VEGF-C. A double-stranded RNA molecule is formed by the complementary pairing between a first RNA portion and a second RNA portion. The length of each portion generally is less than 30 nucleotides in length (e.g., 29, 28, 27, 26, 25, 24, 23, 22, 21, 20, 19, 18, 17, 16, 15, 14, 13, 12, 11, or 10 nucleotides). In some embodiments, the length of each portion is 19 to 25 nucleotides in length. In some siRNA molecules, the complementary first and second portions of the RNA molecule are the "stem" of a hairpin structure. The two portions can be joined by a linking sequence, which can form the "loop" in the hairpin structure. The linking sequence can vary in length. In some embodiments, the linking sequence can be 5, 6, 7, 8, 9, 10, 11, 12 or 13 nucleotides in length. The first and second portions are complementary but may not be completely symmetrical, as the hairpin structure may contain 3' or 5' overhang nucleotides (e.g., a 1, 2, 3, 4, or 5 nucleotide overhang).

RNA molecules have been shown by many researchers to be effective in suppressing mRNA accumulation. siRNA-mediated suppression of nucleic acid expression is specific as even a single base pair mismatch between siRNA and the targeted nucleic acid can abolish the action of RNA interference. siRNAs generally do not elicit anti-viral responses.

There are well-established criteria for designing siRNAs (see, e.g., Elbashire et al., Nature, 411:494 8, 2001; Amarzguioui et al., Biochem. Biophys. Res. Commun., 316:1050 8, 2004; Reynolds et al., Nat. Biotech., 22:326-30, 2004). Details can be found in the websites of several commercial vendors such as Ambion, Dharmacon, GenScript, and OligoEngine. The sequence of any potential siRNA candidate generally is checked for any possible matches to other nucleic acid sequences or polymorphisms of nucleic acid sequence using the BLAST alignment program (see ncbi.nlm.nih.gov on the World Wide Web). Typically, a number of siRNAs have to be generated and screened in order to compare their effectiveness.

Once designed, the siRNAs of the present invention can be generated by any method known in the art, for example, by in vitro transcription, recombinantly, or by synthetic means (e.g., having either a TT or a UU overhang at the 3' end). siRNAs can be generated in vitro by using a recombinant enzyme, such as T7 RNA polymerase, and DNA oligonucleotide templates, or can be prepared in vivo, for example, in cultured cells (see, for example, Elbashir et al., supra; Brummelkamp et al., supra; and Lee et al., Nat. Biotech., 20:500-505, 2002).

In addition, strategies have been described for producing a hairpin siRNA from vectors containing a RNA polymerase III promoter. Various vectors have been constructed for generating hairpin siRNAs in host cells using either an H1-RNA or an snU6 RNA promoter. A RNA molecule as described above (e.g., a first portion, a linking sequence, and a second portion) can be operably linked to such a promoter. When transcribed by RNA polymerase III, the first and second portions form a duplexed stem of a hairpin and the linking sequence forms a loop. The pSuper vector (OligoEngines Ltd., Seattle, Wash.) also can be used to generate siRNA.

A TTTTT penta-nucleotide usually is attached to the end of the second portion (i.e., the antisense strand) in a vector to serve as a terminator for RNA polymerase III transcription. For that reason, siRNA candidates that contain more than three consecutive Ts should be avoided since four or more consecutive Ts in the template nucleic acid triggers termination of RNA polymerase III transcription.

Several techniques can be used to test the effect of different siRNA constructs on cellular mRNA and/or protein levels. For example, dual-GFP transfection, CHO-cell double transfection based on an antibody/epitope specificity, quantitative RT-PCR, Northern blots, Western blots, immunofluorescence, and Hygro/Neo selection. These methods are well known in the art.

Polypeptides

As used herein, the phrase "a ZNF206 polypeptide" refers to a polypeptide at least 10, 11, 12, 12, 14, 15, 20, 30, 40, 49, 50, 100 or more amino acid residues in length and have a high degree of sequence identity with the full-length native, or wild-type, ZNF206 polypeptide or a fragment thereof. Included are variant forms of ZNF206 polypeptides that include deletions, insertions or substitutions of one or more amino acid residues in a native ZNF206 polypeptide sequence, including without limitation polypeptides that exhibit activity similar, but not necessarily identical, to an activity of the full-length native, or wild-type, ZNF206 polypeptide or fragment thereof as measured in a relevant biological assay.

As used herein, the terms "wild-type" or "native" in reference to a peptide or polypeptide are used interchangeably to refer to a polypeptide that has 100% sequence identity with a reference polypeptide that can be found in a cell or organism, or a fragment thereof.

As used herein, the term "ZNF206 activity" refers to a biological activity of a native ZNF206 polypeptide including, but not limited to, repressing PE or PE-like differentiation, regulation of pluripotency gene expression, DNA binding, etc.

As used herein, the terms "peptide" and "oligopeptide" are considered synonymous and, as used herein, each term refers to a chain of at least two amino acids coupled by peptidyl linkages. As used herein, the terms "polypeptide" and "protein" are considered synonymous and each term refers to a chain of more than about ten amino acid residues. All oligopeptide and polypeptide formulas or sequences herein are written from left to right and in the direction from amino terminus to carboxy terminus.

As used herein, the term "isolated" polypeptide or protein refers to a polypeptide or protein removed from its native environment. For example, recombinantly produced polypeptides and proteins expressed in host cells are considered isolated for purposes of the invention as are native or recombinant polypeptides and proteins which have been substantially purified by any suitable technique.

As used herein, the term "binds selectively" is interchangeable with the term "binds specifically, and, when used in reference to a ZNF206 polypeptide, refers to binding of an antibody, ligand, receptor, substrate, or other binding agent to the target ZNF206 polypeptide to a substantially higher degree than to other polypeptides. According to some embodiments, all or substantially all binding of an antibody or other binding agent is to the target ZNF206 polynucleotide, as can be determined given the sensitivity of a particular procedure. An antibody, ligand, receptor, substrate or other binding agent is said to be "selective for" or specific for" a polypeptide or other target molecule, such as ZNF206, if it binds selectively to the target molecule.

The amino acid sequence of a ZNF206 polypeptide or peptide can be varied without significant effect on the structure or function of the protein. In general, it is possible to replace residues which contribute to the tertiary structure of the polypeptide or peptide, provided that residues performing a similar function are used. In other instances, the type of residue may be completely unimportant if the alteration occurs at a non-critical region of the protein.

Thus, the invention further includes variations of ZNF206 polypeptide or peptide that show substantial ZNF206 activity. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Guidance concerning which amino acid changes are likely to be phenotypically silent (i.e., are not likely to have a significant deleterious effect on a function) can be found, for example, in Bowie et al., Science 247:1306-1310, 1990.

Thus, a fragment, derivative or analog of a native, or wild-type ZNF206 polypeptide, may be (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence that is employed for purification of the mature polypeptide or a proprotein sequence.

Charged amino acids may be substituted with another charged amino acid. Charged amino acids may also be substituted with neutral or negatively charged amino acids, resulting in proteins with reduced positive charge. The prevention of aggregation is highly desirable to avoid a loss of activity and increased immunogenicity (Pinckard et al., Clin Exp. Immunol. 2:331-340, 1967; Robbins et al., Diabetes 36:838-845, 1987; Cleland et al., Crit. Rev. Therapeutic Drug Carrier Systems 10:307-377, 1993).

The replacement of amino acids can also change the selectivity of protein binding to cell surface receptors. Ostade et al., Nature 361:266-268 (1993) describes certain mutations resulting in selective binding of TNF-α to only one of the two known types of TNF receptors.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine. Conservative amino acid substitution within the native polypeptide sequence can be made by replacing one amino acid from within one of these groups with another amino acid from within the same group. In one aspect, biologically functional equivalents of the proteins or fragments thereof of the present invention can have ten or fewer, seven or fewer, five or fewer, four or fewer, three or fewer, two, or one conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, J. Mol. Biol. 157:105-132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, J. Mol. Biol. 157:105-132, 1982); these are: isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (4.5). In making such changes, the substitution of amino acids whose hydropathic indices may be within ±2, or ±1, or within ±0.5.

It is also understood in the art that the substitution of like amino acids can be made effectively on the basis of hydrophilicity. U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0.+−0.1), glutamate (+3.0.+−0.1), serine (+0.3), asparagine (+0.2), glutamine (+0.2), glycine (0), threonine (−0.4), proline (−0.5.+−0.1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4). In making changes to a native polypeptide or peptide sequence, the substitution of amino acids whose hydrophilicity values may be within ±2, or within ±1, or within ±0.5.

Of course, the number of amino acid substitutions a skilled artisan would make depends on many factors, including those described above. Generally speaking, the number of substitutions for any given ZNF206 polypeptide will not be more than 50, 40, 30, 20, 10, 5, 3, or 2.

Amino acids in the ZNF206 protein of the present invention that are essential for function can be identified by methods known in the art, such as site-directed mutagenesis or alanine-scanning mutagenesis (Cunningham and Wells, Science 244:1081-1085, 1989). The latter procedure introduces single alanine mutations at every residue in the molecule. The resulting mutant molecules are then tested for biological activity such as in vitro or in vivo ligand or receptor binding or other characteristic biological activities. Sites that are critical for ligand-receptor binding can also be determined by structural analysis such as crystallization, nuclear magnetic resonance or photoaffinity labeling (Smith et al., J. Mol. Biol. 224:899-904, 1992; de Vos et al. Science 255:306-312, 1992).

The polypeptides and peptides of the present invention include native, or wild-type polypeptides and peptides, and polypeptides or peptide variants that are at least 75%, 80%, 85%, 90%, 95%, 96%, 97%, 98% or 99% identical to (or have such a degree of identity with) the native ZNF206 polypeptide and fragments thereof.

By a polypeptide having an amino acid sequence at least, for example, 95% "identical" to a reference amino acid sequence is intended that the amino acid sequence of the polypeptide is identical to the reference sequence except that the polypeptide sequence may include up to five amino acid alterations per each 100 amino acids of the reference amino acid sequence of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide has a particular degree of amino acid sequence identity when compared to a reference polypeptide can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Fragments of the polypeptides described herein may, for example, comprise: the full-length amino acid sequence of ZNF206; a less than full-length amino acid sequence that retains ZNF206 activity; a sequence that comprises one or more antigenic determinants of ZNF206, for example, those that elicit antibodies that bind selectively to ZNF206; etc. Also included are fragments that include both sequences that are unique to ZNF206 and sequences from another protein. The polypeptide fragments of the present invention can be used for numerous purposes, for example, to elicit antibody production in a mammal, as molecular weight markers on SDS-PAGE gels or on molecular sieve gel filtration columns using methods well known to those of skill in the art, etc.

Polypeptides of the present invention can be used to raise, or elicit, polyclonal and monoclonal antibodies that bind selectively to a native ZNF206 polypeptide, which are useful in diagnostic assays for detecting ZNF206 expression or for other purposes. Further, such polypeptides can be used in the yeast two-hybrid system to "capture" binding proteins (Fields and Song, Nature 340:245-246, 1989). For eliciting ZNF206-specific antibody production, the fragment may comprise, for example, a polypeptide of at least 11 amino acids, including at least 4, 5, 6, 7, 8, 9, 10, 11, or more contiguous amino acids of a native ZNF206 polypeptide. Of course, longer fragments with complete sequence homology with the ZNF206 polypeptide, including fragments constituting the full-length ZNF206 polypeptide, may be used for eliciting antibody production. Alternatively, for eliciting ZNF206-specific antibody production, a longer polypeptide may be employed that has at least 70%, or 80%, or 85%, or 90%, or 95%, or 100% amino acid sequence identity to a native ZNF206 polypeptide. Such a longer polypeptide may be at least 15, or 20, or 30, or 40 or more amino acids in length.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998-4002, 1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., Science 219:660-666, 1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective (Sutcliffe et al., supra, at 661).

Antigenic epitope-bearing peptides and polypeptides of the invention are useful for eliciting the production of antibodies, including monoclonal antibodies, which bind selectively to a polypeptide of the invention. A high proportion of hybridomas obtained by fusion of spleen cells from donors immunized with an antigen epitope-bearing peptide generally secrete antibody reactive with the native protein (Sutcliffe et al., supra, at 663). The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for example, Wilson et al., Cell 37:767-778, 1984). The anti-peptide antibodies of the invention also are useful for protein purification, e.g., by adsorption chromatography using known methods.

Antigenic epitope-bearing peptides and polypeptides of the invention designed according to the above guidelines may contain a sequence of at least 7, 8, 9, 10, 11, 12, 13, 14, 15, 20 or 30 or more amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein.

The amino acid sequence of the epitope-bearing peptide may be selected to provide substantial solubility in aqueous solvents (i.e., sequences including relatively hydrophilic residues and highly hydrophobic sequences may be avoided).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by binding studies employing an enzyme-linked immunosorbent assay [ELISA]) in less than four weeks (Houghten, Proc. Natl. Acad. Sci. USA 82:5131-5135, 1985; and U.S. Pat. No. 4,631,211). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously.

Epitope-bearing peptides and polypeptides of the invention are used to induce antibodies according to methods well known in the art. See, for instance, Sutcliffe et al., supra; Wilson et al., supra; Chow et al., Proc. Natl. Acad. Sci. USA 82:910-914; and Bittle et al., J. Gen. Virol. 66:2347-2354, 1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al. (1984), supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 discloses linear $C_{1-7}$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86, 1988). Fusion proteins that have a disulfide-linked dimeric structure due to the IgG part can also be more efficient in binding and neutralizing other molecules than the monomeric ZNF206 protein or protein fragment alone (Fountoulakis et al., J. Biochem. 270:3958-3964, 1995).

Antibodies

ZNF206-selective antibodies for use in the present invention can be raised against the intact ZNF206 or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (or "fragment antibodies") (such as, for example, Fab and F(ab').sub.2 fragments) which are capable of selectively binding to ZNF206. Fab and F(ab') .sub.2 fragments lack the Fc portion of intact antibody, clear more rapidly from the circulation, and may have less non-specific tissue binding of an intact antibody (Wahl et al., J. Nucl. Med. 24:316-325, 1983). Also included are single-chain antibodies.

The antibodies of the present invention may be prepared by any of a variety of methods. For example, cells expressing the ZNF206 or an antigenic fragment thereof can be administered to an animal in order to induce the production of sera containing polyclonal antibodies. In one method, a preparation of ZNF206 protein is prepared and purified as described above to render it substantially free of natural contaminants. Such a preparation is then introduced into an animal in order to produce polyclonal antisera of greater specific activity.

The antibodies of the present invention include monoclonal antibodies (or ZNF206 binding fragments thereof). Such monoclonal antibodies can be prepared using hybridoma technology (Colligan, Current Protocols in Immunology, Wiley Interscience, New York (1990-1996); Harlow and Lane, Antibodies: A Laboratory Manual, Cold Spring Harbor Press, Cold Spring Harbor, N.Y. (1988), Chapters 6-9, Current Protocols in Molecular Biology, Ausubel, infra, Chapter 11). In general, such procedures involve immunizing an animal (for example, a mouse or rabbit) with a ZNF206 antigen or with a ZNF206-expressing cell. Suitable cells can be recognized by their capacity to bind anti-ZNF206 antibody. Such cells may be cultured in any suitable tissue culture medium, such as Earle's modified Eagle's medium supplemented with 10% fetal bovine serum (inactivated at about 56° C.), and supplemented with about 10 µg/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al., Gastroenterology 80:225-232, 1981); Harlow and Lane, infra, Chapter 7. The hybridoma cells obtained through such a selection are then assayed to identify clones which secrete antibodies capable of binding the ZNF206 antigen.

Alternatively, additional antibodies capable of binding to the ZNF206 antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, ZNF206-selective antibodies are used to immunize an animal, such as a mouse. The splenocytes of such an animal are then used to produce hybridoma cells, and the hybridoma cells are screened to identify clones which produce an antibody whose ability to bind to the ZNF206-selective antibody can be blocked by the ZNF206 antigen. Such antibodies comprise anti-idiotypic antibodies to the ZNF206-selective antibody and can be used to immunize an animal to induce formation of further ZNF206-selective antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, ZNF206-binding fragments can be produced through recombinant DNA technology or protein synthesis.

Diagnostic Methods

The present invention provides methods for detecting the presence of ZNF206 polynucleotides (for example, ZNF206 mRNA) or polypeptides in a sample, such as a biological sample from an individual; for quantitating ZNF206 polynucleotides or polypeptides in a sample; for determining a ZNF206/ZNF206 polynucleotide or polypeptide ratio in a sample, etc.

In the methods of the present invention, a measurement of ZNF206 polypeptide or polynucleotide or a ZNF206/ZNF206 ratio is compared to a "reference." Depending on the embodiment of the invention, such a reference can include a measurement in a control sample; a standard value obtained by measurements of a population of individuals; a baseline value determined for the same individual at an earlier timepoint, e.g., before commencing a course of treatment; or any other suitable reference used for similar methods.

As used herein, the term "individual" or "patient" refers to a mammal, including, but not limited to, a mouse, rat, rabbit, cat, dog, monkey, ape, human, or other mammal.

By "biological sample" is intended any biological sample obtained from an individual, including but not limited to, a body fluid, cell, tissue, tissue culture, or other source that contains ZNF206 protein or mRNA. Methods for obtaining such biological samples from mammals are well known in the art.

Detection of mRNA. Total cellular RNA can be isolated from a biological sample using any suitable technique such as the single-step guanidinium-thiocyanate-phenol-chloroform method described in Chomczynski and Sacchi, Anal. Biochem. 162:156-159 (1987). Levels of mRNA encoding ZNF206 are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., Cell 63:303-312, 1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. ZNF206 cDNA labeled according to any appropriate method (such as a $^{32}$P-multiprimed DNA labeling system is used as probe. After hybridization overnight, the filter is washed and exposed to x-ray film. cDNA for use as probe according to the present invention is described in the sections above.

S1 mapping can be performed as described in Fujita et al., Cell 49:357-367, 1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding ZNF206). Northern blot analysis can be performed as described above.

According to one embodiment, levels of mRNA encoding ZNF206 are assayed using a polynucleotide amplification method, including but not limited to a polymerase chain reaction (PCR). One PCR method that is useful in the practice of the present invention is the RT-PCR method described in Makino et al., Technique 2:295-301, 1990), for example. By this method, the radioactivity of the DNA products of the amplification, i.e., the "amplification products" or "amplicons," in the polyacrylamide gel bands is linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding ZNF206 is quantified using an imaging analyzer. RT and PCR reaction ingredients and conditions, reagent and gel concentrations, and labeling methods are well known in the art.

According to one embodiment of an amplification method of the invention, primers are employed that selectively amplify a ZNF206 polynucleotide in a sample, for example, a primer pair including at least one primer that selectively hybridizes to ZNF206 mRNA (e.g., that includes sequences from the region of the ZNF206 mRNA that encodes the ZNF206 polypeptide. The second primer can include any sequence from the target ZNF206 polynucleotide, whether such a sequence is unique to ZNF206 or is shared by ZNF206 and another polynucleotide. This embodiment is useful for amplifying only a ZNF206 transcript (mRNA) in a sample, for example.

According to another embodiment of the invention, primers are employed that selectively amplify a ZNF206 polynucleotide, for example, a primer pair that includes at least one primer that selectively hybridizes to ZNF206 mRNA. The second primer can include any sequence from the target ZNF206 polynucleotide, whether such a sequence is unique to ZNF206 or is shared by ZNF206 and another polynucleotide. This embodiment is useful for amplifying only a ZNF206 transcript (mRNA) in a sample, for example.

According to another embodiment of the invention, primers are employed that amplify both a ZNF206 polynucleotide and a second reference polynucleotide. For example, two primer pairs (e.g., four primers) can be used, one pair that selectively amplifies ZNF206 and a second pair that selectively amplifies the reference polynucleotide, so as to produce amplification products that can be distinguished from one another, for example by length. This embodiment is useful, for example, for determining the ratio of ZNF206 mRNA to a reference mRNA in a sample.

The skilled artisan will be able to produce additional primers, primer pairs, and sets of primers for PCR and other amplification methods based on the sequences taught herein.

One embodiment of the present invention is a kit that includes primers useful for amplification methods according to the present invention. Such kits also include suitable packaging, instructions for use, or both.

Another PCR method useful for detecting the presence of and/or quantitating ZNF206 mRNA and protein in a biological sample is through the use of "bio-barcode" nanoparticles. For detection and/or quantitation of proteins, for example, two types of capture particles are employed: one is a micro-size magnetic particle bearing an antibody selective for a target protein, and the other is a nanoparticle with attached antibodies selective for the same protein. The nanoparticle also carries a large number (e.g., ~100) of unique, covalently attached oligonucleotides that are bound by hybridization to complementary oligonucleotides. The latter are the "bio-barcodes" that serve as markers for a selected protein. Because the nanoparticle probe carries many oligonucleotides per bound protein, there is substantial amplification, relative to protein. There is a second amplification of signal in a silver enhancement step. The result is 5-6 orders of magnitude greater sensitivity for proteins than ELISA-based assays, by detecting tens to hundreds of molecules. See, e.g., U.S. Pat. No. 6,974,669. See also, e.g., Stoeva et al., J. Am. Chem. Soc. 128:8378-8379, 2006, for an example of detection of protein cancer markers with bio-barcoded nanoparticle probes. The bio-barcode method can also be used for detecting and/or quantitating mRNA and other polynucleotides in a sample (Huber et al., Nucl. Acids Res. 32:e137, 2004; Cheng et al., Curr. Opin. Chem. Biol. 10:11-19, 2006; Thaxton et al., Clin. Chim. Acta 363:120-126, 2006; U.S. Pat. No. 6,974,669).

Detection of Polypeptide. Assaying the presence of, or quantitating, ZNF206 polypeptide in a biological sample can occur using any method known in the art.

Antibody-based techniques are useful for detecting the presence of and/or quantitating ZNF206 levels in a biological sample. For example, ZNF206 expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of ZNF206 for Western-blot or dot/slot assay (Jalkanen et al., J. Cell. Biol. 101:976-985, 1985; Jalkanen et al., J. Cell. Biol. 105:3087-3096, 1987). In this technique, which is based on the use of cationic solid phases, quantitation of ZNF206 can be accomplished using isolated ZNF206 as a standard. This technique can also be applied to body fluids. With these samples, a molar concentration of ZNF206 will aid to set standard values of ZNF206 content for different tissues, fecal matter, body fluids (serum, plasma, urine, synovial fluid, spinal fluid), etc. The normal appearance of ZNF206 amounts can then be set using values from healthy individuals, which can be compared to those obtained from a test subject.

Other antibody-based methods useful for detecting ZNF206 levels include immunoassays, such as the enzyme linked immunosorbent assay (ELISA), the radioimmunoassay (RIA), and the "bio-barcode" assays described above. For example, ZNF206-selective monoclonal antibodies can be used both as an immunoadsorbent and as an enzyme-labeled probe to detect and quantify the ZNF206. The amount of ZNF206 present in the sample can be calculated by reference to the amount present in a standard preparation using a linear regression computer algorithm. Such an ELISA for detecting a tumor antigen is described in Iacobelli et al., Breast Cancer Research and Treatment 11:19-30, 1988. In another ELISA assay, two distinct selective monoclonal antibodies can be used to detect ZNF206 in a sample. In this assay, one of the antibodies is used as the immunoadsorbent and the other as the enzyme-labeled probe.

The above techniques may be conducted essentially as a "one-step" or "two-step" assay. The "one-step" assay involves contacting ZNF206 with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase, for example, has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc), and fluorescent labels, such as fluorescein and rhodamine, and biotin.

In addition to assaying ZNF206 levels in a biological sample obtained from an individual, ZNF206 can also be detected in vivo by imaging. Antibody labels or markers for in vivo imaging of ZNF206 include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A ZNF206-selective antibody or antibody fragment which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain ZNF206. In vivo tumor imaging is described in Burchiel et al., "Immunopharmacokinetics of Radiolabeled Antibodies and Their Fragments" (Chapter 13 in Tumor Imaging: The Radiochemical Detection of Cancer, Burchiel and Rhodes, eds., Masson Publishing Inc., 1982).

Where in vivo imaging is used to detect enhanced levels of ZNF206 for diagnosis in humans, one may use "humanized" chimeric monoclonal antibodies. Such antibodies can be produced using genetic constructs derived from hybridoma cells producing the monoclonal antibodies described above. Methods for producing chimeric antibodies, including humanized chimeric antibodies, are known in the art. See, for review, Morrison, Science 229:1202, 1985; Oi et al., BioTechniques 4:214, 1986; Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643, 1984; Neuberger et al., Nature 314: 268, 1985.

Further suitable labels for the ZNF206-selective antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{09}$Pd, etc. $^{111}$In has advantages where in vivo imaging is used since its avoids the problem of dehalogenation of the $^{125}$I- or $^{131}$I-labeled monoclonal antibody by the liver. In addition, this radionucleotide has a more favorable gamma emission energy for imaging (Perkins et al., Eur. J. Nucl. Med. 10:296-301, 1985); Carasquillo et al., J. Nucl. Med. 28:281-287, 1987). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870, 1987).

Examples of suitable non-radioactive isotopic labels include $^{157}$Gd, $^{55}$Mn, $^{162}$Dy, $^{52}$Tr, and $^{56}$Fe.

Examples of suitable fluorescent labels include $^{152}$Eu label, fluorescein, isothiocyanate, rhodamine, phycoerythrin, phycocyanin, allophycocyanin, o-phthaldehyde, and fluorescamine.

Examples of suitable toxin labels include diphtheria toxin, ricin, and cholera toxin. Examples of chemiluminescent labels include luminal, isoluminal, aromatic acridinium ester, imidazole, acridinium salt, oxalate ester, luciferin, luciferase, and aequorin.

Examples of nuclear magnetic resonance contrasting agents include heavy metal nuclei such as Gd, Mn, and Fe.

Typical techniques for binding the above-described labels to antibodies are provided by Kennedy et al. (Clin. Chim. Acta 70:1-31, 1976), and Schurs et al. (Clin. Chim. Acta 81:1-40, 1977). Coupling techniques mentioned in the latter are the glutaraldehyde method, the periodate method, the dimaleimide method, the m-maleimidobenzyl-N-hydroxy-succinimide ester method.

Diagnosing Disease States Resulting From Mutations in ZNF206

Given the effect of ZNF206 on the pluripotency of a cell, mutations in ZNF206 may result in an aberrant pluripotency state in a cell, leading to cancerous or other disease states. According to one embodiment of the invention, methods are provided for diagnosing a disease state resulting from a mutation in a ZNF206 polynucleotide comprising (a) providing a sample from a patient comprising a cell and (b) determining whether the sample comprises a mutated ZNF206 polynucleotide. The presence of a mutated ZNF 206 polynucleotide in the sample may be determined, for example by: contacting the sample with a polynucleotide probe or primer that hybridizes specifically to a mutated ZNF206 polynucleotide sequence; by contacting the sample with one or more primers that comprise a polynucleotide sequence that hybridizes selectively to the mutated ZNF206 polynucleotide, and performing an amplification reaction (e.g., a PCR or bio-barcode assay) to produce an amplification product that indicates the presence of the mutated ZNF206 polynucleotide in the sample; by detecting a restriction fragment length polymorphism; or by contacting the sample with an antibody probe that hybridizes specifically to a mutated ZNF polypeptide sequence encoded by the mutated ZNF polynucleotide.

Pharmaceutical Compositions and Methods

The Oct3/4 gene, a POU (Pit-Oct-Unc) family of transcription factors was once thought to be expressed only in embryonic stem cells and in tumor cells. With the availability of normal adult human stem cells, tests for the expression of Oct3/4 gene and the stem cell theory in human carcinogenesis became possible. Human breast, liver, pancreas, kidney, mesenchyme, and gastric stem cells, HeLa and MCF-7 cells, and canine tumors were tested with antibodies and polymerase chain reaction (PCR) primers for Oct3/4. Adult human breast stem cells, immortalized nontumorigenic and tumor cell lines, but not normal differentiated cells, expressed Oct3/4. Adult human differentiated cells lose their Oct-4 expression. Oct3/4 is expressed in a few cells found in the basal layer of human skin epidermis. The data demonstrate that normal adult stem cells and cancer stem cells maintain expression of Oct3/4, consistent with the stem cell hypothesis of carcinogenesis. These Oct-4-positive cells may represent "cancer stem cells." (Carcinogenesis, 26:495-502, 2005). One therapeutic strategy is to suppress the Oct-4 gene in order to cause such "cancer stem cells" to differentiate.

Expression of a ZNF206-encoding construct in an ESC is a way of maintaining the cell in a pluripotent state and preventing differentiation of the ESC, particularly default differentiation towards the extra-embryonic lineage. In fact, ZNF206 expression in differentiated cells may be used to "reprogram" such cells to become pluripotent. The ability to reduce ZNF206 expression, and thereby promote the differentiation of pluripotent cells has pharmaceutical applications. Reducing ZNF206 expression may be used to treat certain cancers, or to reduce the risk of developing a cancer, characterized by cells that that have elevated levels of ZNF206 expression. In support of this approach, pluripotent stem cells were induced from mouse embryonic or adult fibroblasts by introducing stem cell transcription factors Oct 3/4, SOX2, c-Myc and Klf4 (Takahashi and Yamanka, Cell 126:663-676, 2006; Wernig et al., In vitro reprogramming of fibroblasts into a pluripotent ES-cell-like state, Nature advance online publication 6 Jun. 2007 [doi:10.1038/nature05944]; Okita et al., Generation of germline-competent induced pluripotent stem cells, Nature advance online publication 6 Jun. 2007 [doi: 10.1038/nature05934]). ZNF could be used to induce pluripotent stem cells from human embryonic or adult cells, such as, for example, fibroblast cells, by itself or in combination with one or more stem cell transcription factors such as Oct 3/4, SOX2, c-Myc or Klf4, for example, under ES cell culture conditions.

The invention will be better understood by reference to the following Examples, which are intended to merely illustrate the best mode now known for practicing the invention. The scope of the invention is not to be considered limited thereto.

EXAMPLE 1

Materials and Methods

Human Embryonic Stem Cell (hESC) Culture. hESC lines WA01 (H1) and WA09 (H9) (WiCell, Madison Wis.) were initially maintained on irradiated mouse embryonic fibroblast (MEF) feeder cells in medium that consisted of DMEM/F-12 (80%), Knockout Serum Replacement (20%), L-alanyl-L-glutamine (GlutaMax; 2 mM), MEM nonessential amino acids (1×), b-Mercaptoethanol (100 mM) (all from Invitrogen, Carlsbad, Calif.), and bFGF (4 ng/ml) (PeproTech Inc., Rocky Hill, N.J.) as described previously (Thomson et al., 1998), then transferred to human feeder layers (HS27 line, ATCC). For feeder-free growth, cells were transferred to Matrigel (growth factor-reduced, Becton Dickinson, Bedford, Mass.) or human purified laminin-coated dishes, and cultured in the same medium with a higher concentration of bFGF (20 ng/ml). HESCs were mechanically passaged every 5 to 7 days by cutting undifferentiated hESC colonies into small pieces using a 27 G PrecisionGlide Needle attached to a 1 ml syringe (Becton Dickinson, Bedford, Mass.).

Isolation of hESC-Derived PEL Cells. WA09 hESC-derived PEL cells were isolated from the differentiated cells surrounding the periphery of undifferentiated hESC colonies grown in feeder-free defined culture. A two-step mechanical/enzymatic treatment method was employed: first, all of the morphologically distinct hESC colonies were mechanically dissected away from the cultures, then the remaining cells were lifted by brief treatment with 0.05% trypsin and then transferred to new Matrigel- or laminin-coated plates containing hESC medium. The PEL cells were further purified by repeating the isolation procedure multiple times until no morphologically hESC-like cells were observed. POU5F1/OCT4 staining confirmed that no positive cells remained and GATA6 staining showed that the PEL cells homogeneously expressed this marker. The PEL cells maintained a normal diploid karyotype identical to the parental hESC cells for at least 20 passages. For production of feeder layers, PEL cells were irradiated in the same manner as human fibroblast cell lines.

Production of Lentivirus Particles and Infection of hESCs. Briefly, lentiviral vectors were produced by co-transfecting the transfer vector pFUGW, the HIV-1 packaging vector 8.9, and the VSVG envelope glycoprotein into 293 fibroblasts and concentrated as described previously. Undifferentiated hESCs (line WA01 [passage 49] and line WA09 [passage 45]) that had been growing in feeder-free culture for 4 days were incubated with lentiviral vector particles and polybrene (6 µg/ml; Sigma) overnight and the medium was changed the next day. After 7 days of continuous culturing in the defined conditions, hESC colonies that displayed homogenous expression of eGFP were each mechanically picked and individually transferred to wells of 6 well plates. The eGFP-positive undifferentiated hESC subcultures were maintained under the defined culture conditions. For testing growth of colonies from single cells, eGFP-positive colonies were dissociated and sorted by FACS into 96 well plates (see below). Colonies that were observed to be derived from single cells were expanded and characterized.

Fluorescence Activated Cell Sorting (FACS) and Single-Cell Culture. Undifferentiated eGFP-hESCs were dissociated with 0.05% trypsin/0.53 mM EDTA (Invitrogen) into a suspension of single cells and small clusters. Dissociated cells were filtered through 85-µm Nitex mesh to remove aggregates and then sorted on a FACSVantage SE equipped with DiVa electronics and software (Becton Dickinson Biosciences). The GFP signal was excited with an argon laser tuned to 488 nm at 200 mW of power and the emission signal was collected through a 530/30 bandpass filter. The eGFP-positive cells were sorted into wells of a 96 well plate (1 eGFP cell/well) at 15 psi using a 100-µm nozzle tip. Propidium iodide was used to exclude dead cells and only live cells were used for sorting. PEL cell conditioned medium was generated by 48 hours incubation at 37° C. in serum-free medium containing ITS supplement (Invitrogen) and 100 ng/ml bFGF but no serum or serum replacement. Colony-forming efficiency was measured by plating a known number of cells (1000) into 6-well dishes containing the appropriate feeder layer or conditioned medium.

Microarray Analysis. RNA was isolated from cultured cells using the Qiagen RNEasy kit (Qiagen, Inc, Valencia, Calif.). Two PEL cultures, 2 undifferentiated hESC (WA09) cultures, and 2 HS27 human foreskin fibroblast (HFF) cultures were harvested separately and served as biological replicates. To assure that only undifferentiated hESCs were isolated, colonies were isolated by hand using a micropipette. Sample preparation and analysis was performed as previously described (Cai et al., Stem Cells 24:516-530, 2006; Schwartz et al., Stem Cells Dev. 14:517-534, 2005). Briefly, amplification was performed using 100 ng of total RNA using the Illumina RNA Amplification kit (Ambion, Inc., Austin, Tex.) following the manufacturer's instructions; labeling was done by incorporating of biotin-16-UTP (Perkin Elmer Life and Analytical Sciences, Boston, Mass.) present at a ratio of 1:1 with unlabeled UTP. Labeled, amplified material (700 ng per array) was hybridized to the Illumina Sentrix Human 6 BeadChip according to the manufacturer's instructions (Illumina, Inc., San Diego, Calif.). Arrays were washed, and then stained with Amersham fluorolink streptavidin-Cy3 (GE Healthcare Bio-Sciences, Little Chalfont, UK) according to methods provided by the manufacturer. Arrays were scanned with an Illumina BeadArray Reader confocal scanner and array data processing and analysis were performed using Illumina BeadStudio software. The Illumina BeadArrays have an average of 30 beads of each type (50-mer complementary oligonucleotides) in each array, so for each set of biological replicates we obtained approximately 60 independent measurements of hybridization for each transcript. Differential expression of individual genes between groups was calculated by the t-test.

RT-PCR. Expression of several gene transcripts was probed by semiquantitative RT-PCR. Initial denaturation was carried out at 94° C. for 2 minutes, followed by 35 cycles of PCR (94° C. for 30 seconds, 55° C. for 30 seconds, 72° C. for 1 minute). Primers used and their expected products are (SEQ ID NOS 1-28, respectively in order of appearance):

| Product | Size (bp) | Primers |
| --- | --- | --- |
| Activin A (Inhibin beta A) | 262 | 5'-CTTGAAGAAGAGACCCGAT-3' <br> 5'-CTTCTGCACGCTCCACTAC-3' |
| Activin Receptor IIB (ACTRIIB-2B) | 556 | 5'-ACACGGGAGTGCATCTACTACAACG-3' <br> 5'-TTCATGAGCTGGGCCTTCCAGACAC-3'; |
| AFP | 676 | 5'-AGAACCTGTCACAAGCTGTG-3' <br> 5'-CACAGCAAGCTGAGGATGTC-3' |
| beta-Actin | 400 | 5'-TGGCACCACACC TTTCTACAATGAGC-3' <br> 5'-GCACAGCTTCTCCTTAA TGTCACGC-3' |
| CDX2 | 563 | 5'-GAACCTGTGCGAGTGGATGCG-3' <br> 5'-GGTCTATGGCTGTGGGTGGGAG-3' |
| DNMT3B | 433 | 5'-CTCTTACCTTACCATCGACC-3' <br> 5'-CTCCAGAGCATGGTACATGG-3' |
| GATA4 | 218 | 5'-CATCAAGACGGAGCCTGGCC-3' <br> 5'-TGACTGTCGGCCAAGACCAG-3' |
| HNF4 | 762 | 5'-GCTTGGTTCTCGTTGAGTGG-3' <br> 5'-CAGGAGCTTATAGGGGCTCAGAC-3' |
| LIN-28 | 420 | 5'-AGTAAGCTGCACATGGAAGG-3' <br> 5'-ATTGTGGCTCAATTCTGTGC-3' |
| SOX2 | 370 | 5'-CCGCATG TACAACATGATGG-3' <br> 5'-CTTCTTCATGAGCGTCT TGG-3' |
| GATA-6 | 213 | 5'-CCATGACTCCAACTTCCACC-3' <br> 5'-ACGGAGGACGTGACTTCGGC-3' |
| NANOG | 493 | 5'-GGCAAACAACCCACTTCTGC-3' <br> 5'-TGTT CCAGGCCTGATTGTTC-3' |
| POU5F1 | 247 | 5'-CGTGAAGCTGGAGAAGGAGAAGCTG-3' <br> 5'-CAAGGGCCGCAGCTTACACATGTTC-3' |
| SOX 17 | 181 | 5'-CGCACGGAATTTGAACAGTA-3' <br> 5'-GGATCAGGGACCTGTCACAC-3' |

Immunocytochemistry. Cultures were fixed with 4% paraformaldehyde and blocked in 1×PBS containing 0.2% Triton X-100 and 2% BSA. The cells were incubated with the primary antibody in 0.1% Triton X-100 in PBS at 4° C. overnight. Then, secondary antibody (Invitrogen) was added and incubated at RT for 45 min. After staining with DAPI, cells were visualized with a fluorescence microscope. Primary antibody to AFP, GATA6, POU51/OCT4, SSEA-4, and Tra-1-81 were obtained from Santa Cruz Biotechnology.

Teratoma Formation. Approximately $10^4$ hESCs were injected beneath the kidney capsule of adult male Severe Combined Immunodeficient (SCID) mice. After 21 to 90 days, mice were sacrificed and teratomas were dissected, fixed in Bouin's fixative overnight, processed for paraffin sections and stained with hematoxylin and eosin. Sections were examined for evidence of tissue differentiation using bright field light microscopy and photographed as appropriate. All procedures involving mice were carried out in accordance with Institutional and NIH guidelines.

Results

Identification of ZNF206 as a Potential Transcriptional Repressor of PE-Like Differentiation. The molecular mechanisms regulating early lineage commitment from the ICM (or its in vitro counterpart, the human embryonic stem cell [hESC]) to primitive endoderm (PE) are poorly understood. NANOG is the only known transcription factor that regulates hESC self-renewal by inhibiting PE differentiation.

Figure 2A:
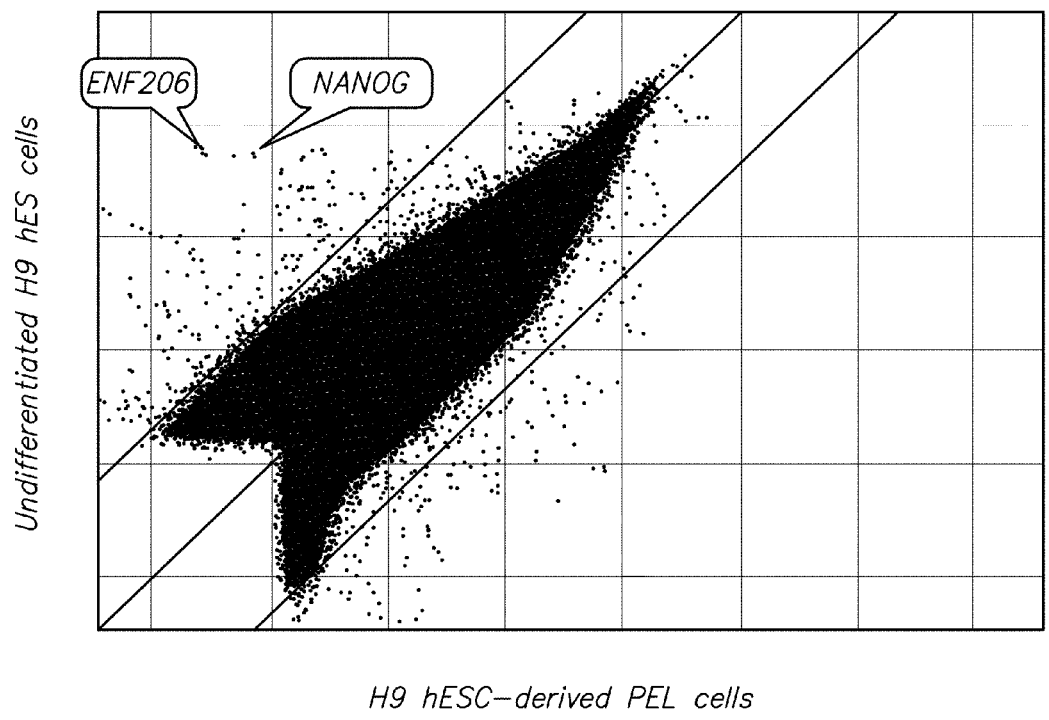
FIG. 2 shows high and unique expression of ZNF206 in undifferentiated hESCs. [A] ZNF206 and NANOG were highly expressed in hESC line WA09 (H9) but not in PE-like (PEL) cells derived from them. [B] Quantitative RT-PCR analysis of ZNF206 expression in H9 hESCs, in PEL cells derived from H9 hESCs, and in adult human tissues.

To identify other transcription factors that could act as specific repressors of the PE (with similar proprieties as NANOG) we performed microarray analysis on an isolated population of hESC derived PE-like (PEL) cells and on their parental undifferentiated clonally-related hESC line. From these analyses, we found many genes that were uniquely expressed in hESCs and not expressed in PEL cells. Among the many genes that exhibited unique expression was a zinc finger protein (ZNF206) and NANOG (FIG. 2A).

Figure 2B:
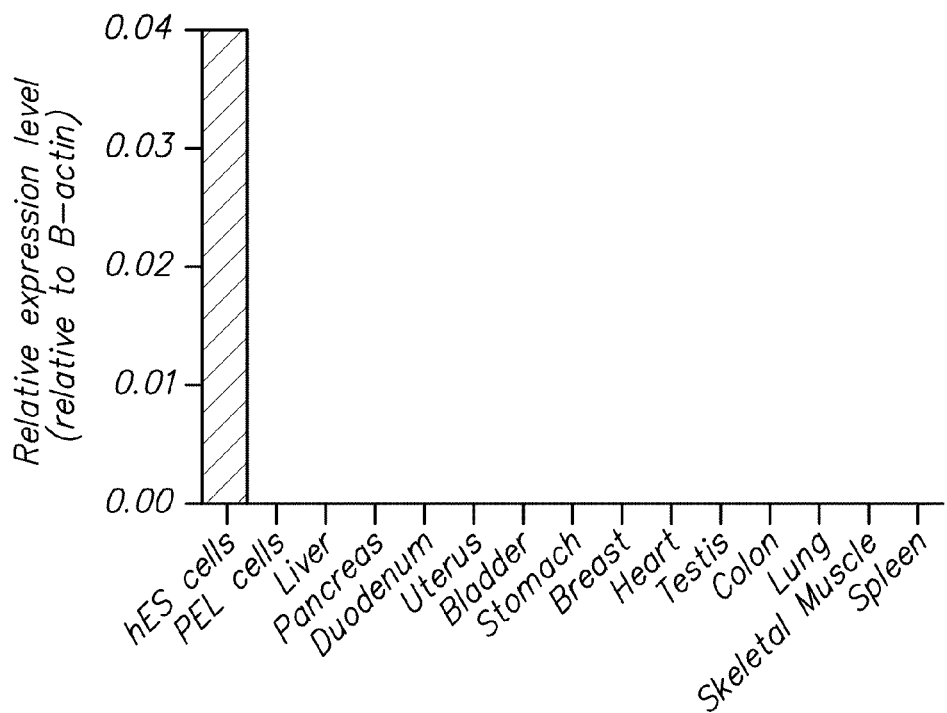

The identification of NANOG among the genes uniquely expressed in undifferentiated hESCs offered us confidence that our microarray analysis had, indeed, revealed genes that might be involved in regulating self-renewal and early lineage commitment to the PE. Since our goal was to find novel transcription factors that might act as transcriptional repressors, we decided to focus on ZNF206 since zinc finger proteins often act as transcriptional regulators. Therefore, we hypothesized that it may be a novel repressor of PE (or PE-like) differentiation. To determine whether ZNF206 is uniquely expressed in hESCs, we performed quantitative RT-PCR on many human tissues and found it to be expressed only in hESCs and not in differentiated PEL cells or any of the differentiated human tissues tested (FIG. 2B).

Figure 3A:
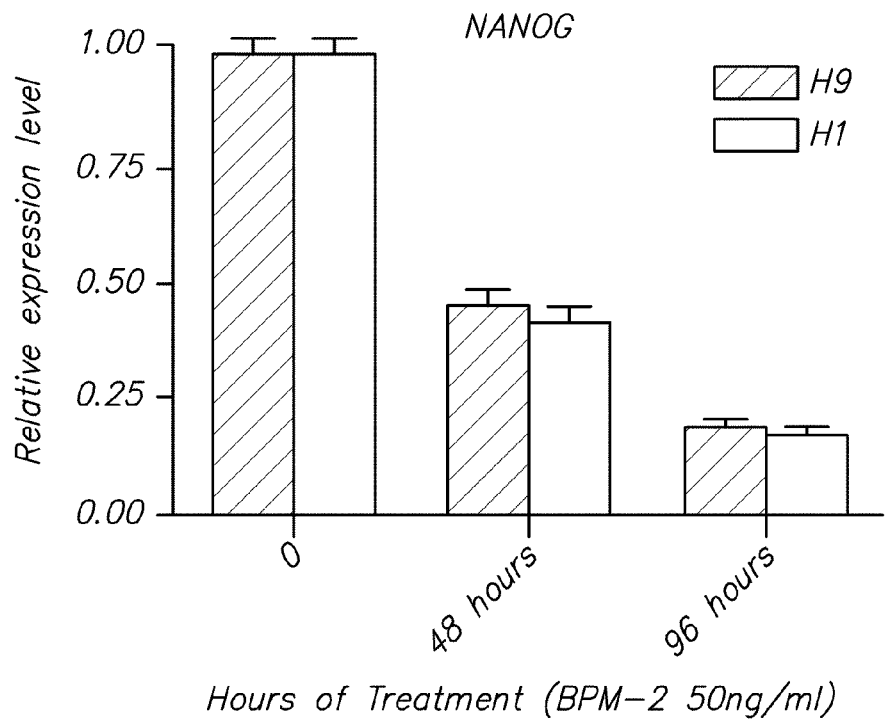
FIG. 3 shows that ZNF206 expression is downregulated upon hESC differentiation into extraembryonic endoderm cells. HESCs (from lines WA09 [H9] and WA01 [H1]) were treated for various times—0, 48, 96 hrs—with BMP2 (50 ng/ml) followed by Quantitative RT-PCR to analyze the expression of NANOG [A], ZNF206 [B], GATA6 [C], and GATA4 [D].
Figure 3B:
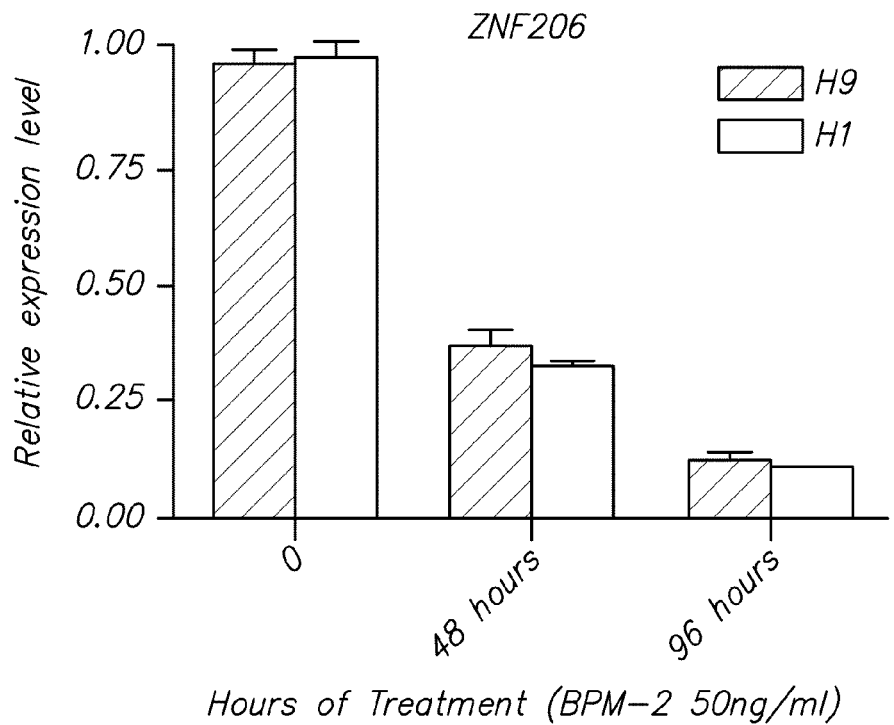
Figure 3C:
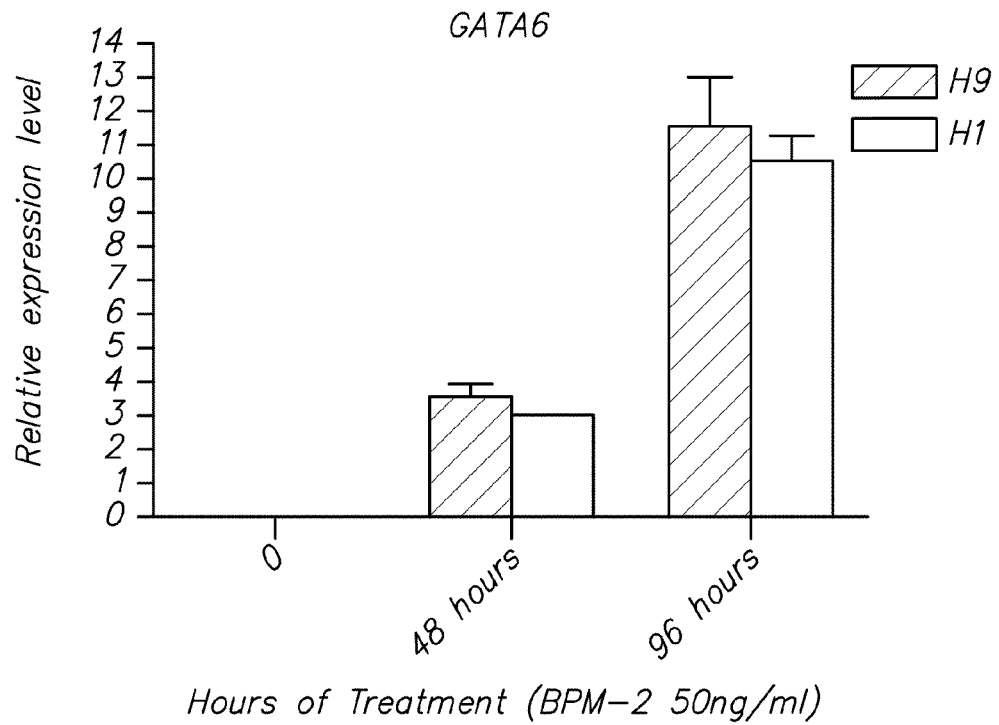
Figure 3D:
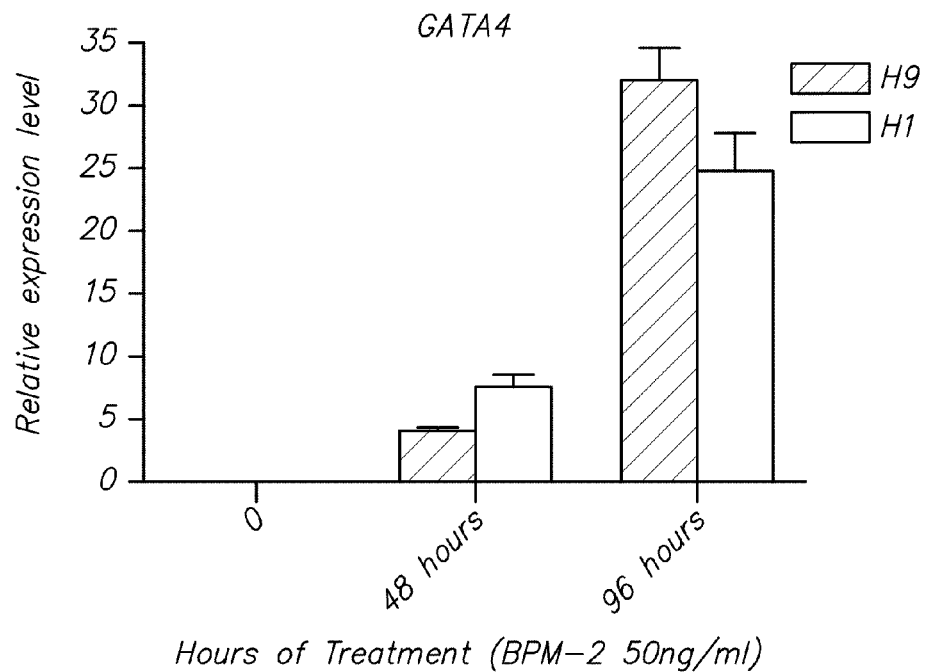

To test further whether ZNF206 expression is regulated during early differentiation into the PE, we treated hESCs with BMP2, a factor previously reported to induce hESCs to differentiate into PE (Pera et al., J. Cell Sci. 117:1269-1280, 2004). Indeed, NANOG and ZNF206 expression were both down-regulated in BMP2-treated hESCs (FIGS. 3A and 3B) while expression of PE markers GATA6 and GATA4 were induced (FIGS. 3C and 3D). The similarity in the expression patterns of NANOG and ZNF206 suggested to us that ZNF206 may have a similar function as NANOG in promoting self-renewal by inhibiting PE differentiation.

Figure 4A:
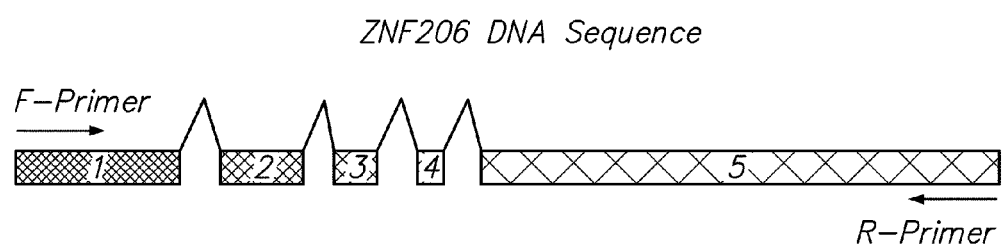
FIG. 4 shows the predicted protein sequence of three isoforms of ZNF206. The ZNF206 gene contains five introns and five exons. [A] Primers were specifically designed to amplify and to clone the different spliced ZNF206 mRNA isoforms expressed in undifferentiated hESCs. [B] Four different ZNF206 mRNA isoforms were cloned from undifferentiated hESCs. Isoform 1 is 2568 bp, isoform 2 is 2343 bp, and isoform 3 is 2075 bp. [C] Isoform 1 (SEQ ID NO: 29) and 4 (SEQ ID NO: 32) are predicted to encode truncated ZNF206 proteins containing a "Novel" and "SCAN" domain. The Novel domain contains a sumoylation site and the SCAN domain has been previously reported to mediate protein-protein interactions. On the other hand, ZNF206 isoform 2 (SEQ ID NO: 30) is predicted to contain 780 amino acids containing the Novel, SCAN and 14 C2H2 Zinc finger domains. The C2H2 zinc finger domains often mediate DNA binding. ZNF206 isoform 3 disclosed as SEQ ID NO: 31.
Figure 4B:
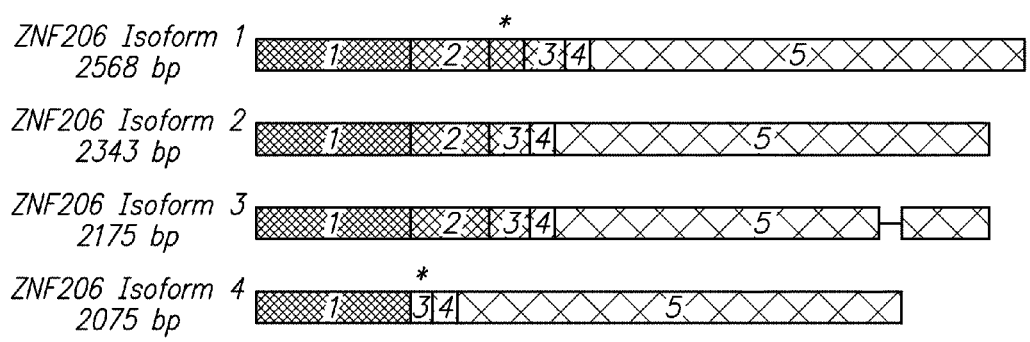

Human ZNF206 Cloning and Expression Analysis. FIG. 4 shows the predicted protein sequence of three isoforms of ZNF206. The ZNF206 gene contains five introns and five exons. To begin to understand the function of human ZNF206, primers were specifically designed to amplify and to clone the different spliced ZNF206 mRNA isoforms expressed in undifferentiated hESCs by RT-PCR (FIG. 4A). Four different ZNF206 mRNA isoforms were cloned from undifferentiated hESCs; isoform 1 is 2568 bp, isoform 2 is 2343 bp, and isoform 3 is 2075 bp (FIG. 4B). These isoforms likely result from alternative splicing that takes place in undifferentiated hESCs. The ZNF206 isoform 2 is predicted encode the 780 amino-acid full-length functional ZNF206 protein that contains the Novel and SCAN domains and 14 $C_2H_2$ zinc fingers (FIG. 4C). The Novel domain contains a sumoylation site, and the SCAN domain has been previously reported to mediate protein-protein interactions. Zinc fingers often mediate DNA binding. ZNF206 isoform 3 is predicted to encode a protein that contains a SCAN domain and 13 $C_2H_2$ zinc fingers (FIG. 4C). ZNF206 isoforms 1 and 4 are predicted to encode short truncated proteins containing the Novel and SCAN domains but lacking the 14 $C_2H_2$ zinc finger domains (FIG. 4C).

Figure 5:
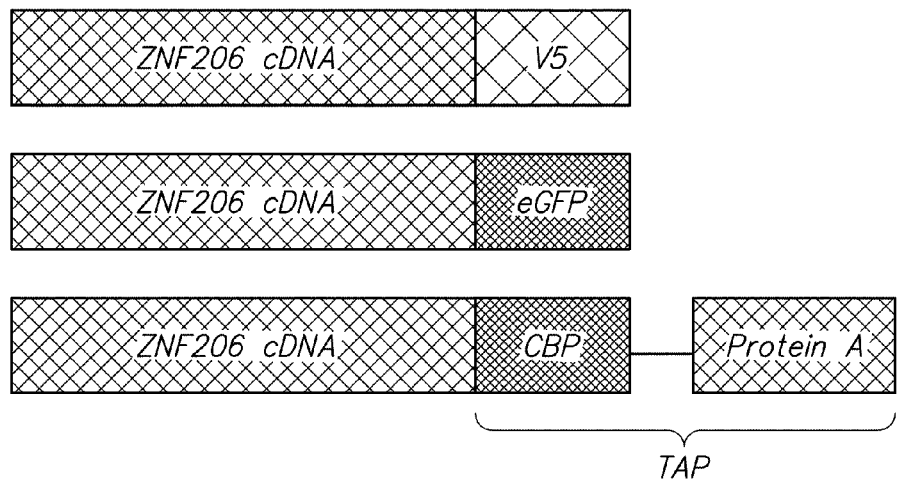
FIG. 5 shows a diagram of three C-terminally tagged ZNF206 lentivirus expression vectors that we have successfully made.

The ZNF206 mRNA transcripts for the four isoforms are similar in size; however isoform 2 is the predominant form expressed by undifferentiated hESCs. As a result, we focused on ZNF206 isoform 2 and generated various ZNF206 lentivirus expression constructs containing different C-terminal tags, one a V5 tag, another a eGFP fluorescent protein, and third containing a TAP tag (FIG. 5). To begin analyzing the localization of ZNF206 protein, we transfected human 293T kidneys cells and human cervical HeLa cells with lentiviral vectors expressing ZNF206-eGFP and ZNF206-V5 protein. Our expression experiments show that both the ZNF206-eGFP and the ZNF206-V5 tagged protein localizes to the nucleus.

Figure 6A:
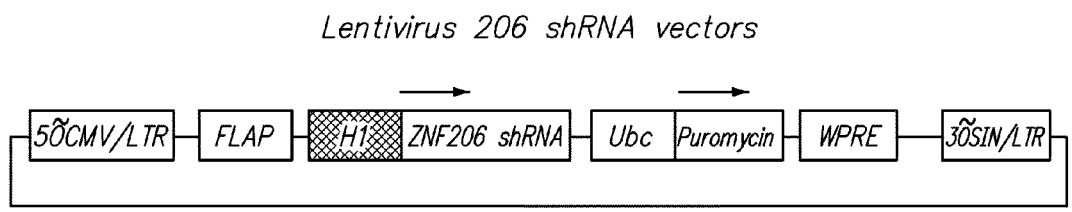
FIG. 6 shows the knock-down efficiency of lentiviral ZNF206 shRNA expression constructs. Human kidney 293FT-ZNF206-V5 expressing cell lines were infected with lentiviral particles containing ZNF206 shRNA expression constructs. After puromycin selection and expansion of infected 293FT cells, we performed quantitative RT-PCR [A] and Western blot analysis [B].

Knockdown of ZNF206 Protein Causes the Down-Regulation of Pluripotency Genes in hESCs. To determine the functional role of ZNF206 in hESCs, we decided to knockdown its expression in undifferentiated hESCs by expressing short hairpin RNAs (shRNAs) specifically directed against the human ZNF206 mRNA. Sense and antisense oligos for ZNF206 shRNA were annealed to form a linker for ligation into pEN_H1 Entry vector. We successfully generated three gateway entry clones. Each candidate ZNF206 shRNA clone was fully sequenced to ensure that they retained 100% homology to the ZNF206 target gene. The H1 Pol III-ZNF206 Cassettes were then subcloned into the lentiviral expression construct pDSL_hpUGIP (a shRNA lentiviral expression destination vector obtained from ATTC) via the Gateway LR recombination reaction (Invitrogen) (FIG. 6A). We then tested their ability to specifically knockdown the expression of ZNF206 in 293FT-ZNF206-V5 expressing cells and performed quantitative RT-PCR and Western blot analysis using an anti-V5 antibody (Invitrogen). The V5 antibody recognizes the C-terminal V5 epitope of the ZNF206-V5 fusion protein and allowed us to see the protein knock-down efficiency. Our results indicated that two lentiviral shRNA constructs specifically down-regulated ZNF206 mRNA and protein expression but only the lentiviral shRNA ZNF206 C expression construct was effective at down-regulating ZNF206 protein at >90% (FIG. 6A, B).

To evaluate endogenous ZNF206 expression in undifferentiated hESC's we generated a custom rabbit polyclonal anti-peptide polyclonal antibody raised against amino acids 711-726 of human ZNF206 protein sequence (FIG. 7A) we found that this antibody specifically detected a protein that was approximately 80 kD in undifferentiated hESC's and not in the hESC-derived PEL differentiated cells, corresponding to the predicted full size of the human ZNF206 protein.

Figure 8:
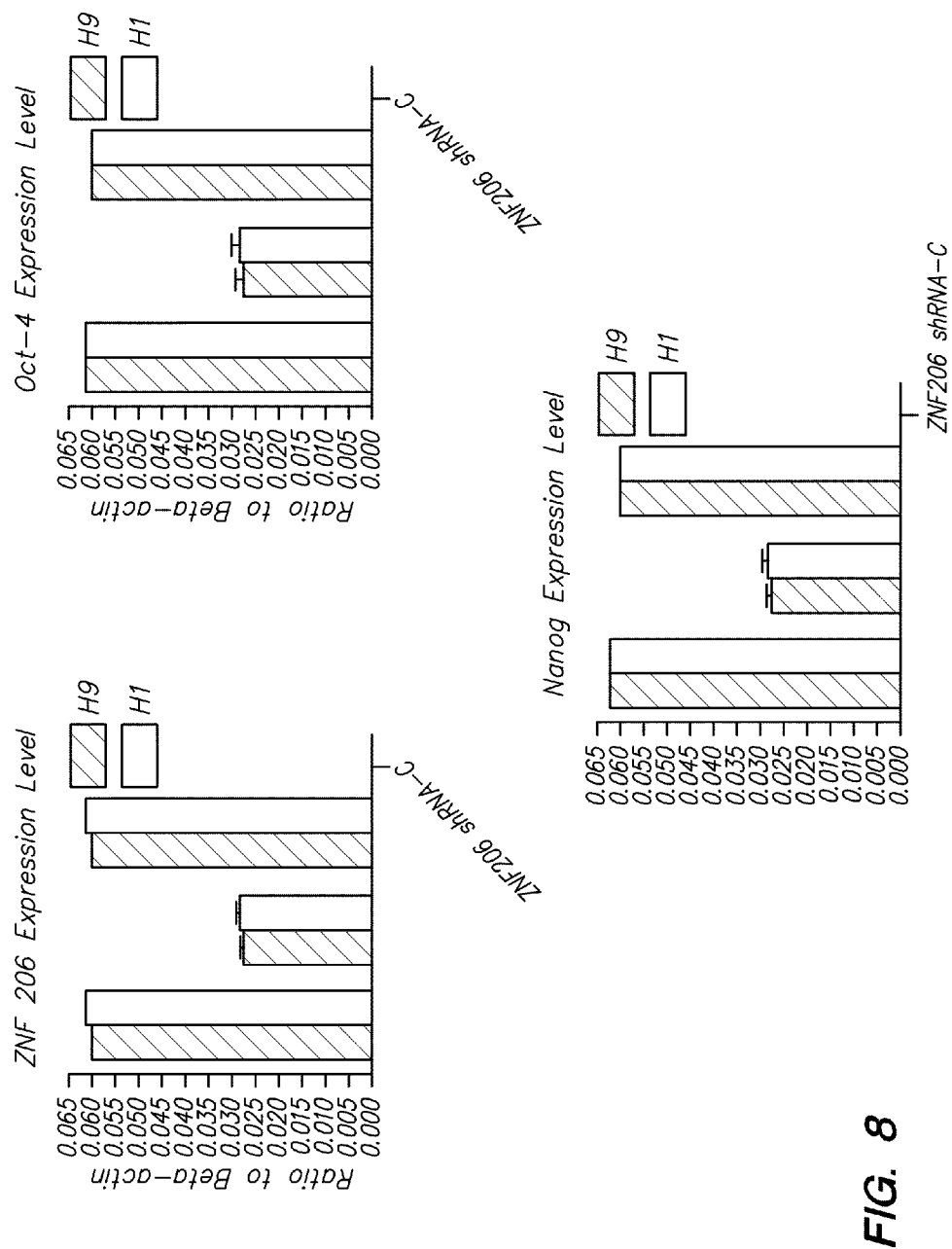
FIG. 8 shows the effects of ZNF206 knockdown on OCT-4 and NANOG expression in hESCs. hESCs were infected with three different shRNA lentiviral expression particles (ZNF206 shRNA-A, ZNF206 shRNA-B, ZNF206 shRNA-C) and the control lentiviral empty vector. Four days after infection of undifferentiated hESC lines H9 (WA09) and H1 (WA01), the mRNA and protein expression of ZNF206, Oct-4 and NANOG were determined by quantitative RT PCR.

To evaluate the effects of ZNF206 down-regulation, we infected undifferentiated H9 (NIH WA09) and H1 (NIH WA01) hESC lines with three different ZNF206 shRNA lentivirus expression particles (ZNF 206 shRNA-A, ZNF 206 shRNA-B, or ZNF 206 shRNA-C) or lentivirus carrying "empty" control vectors. Four days after infection of undifferentiated hESCs, we evaluated their effects on ZNF206, OCT-4, and NANOG mRNA levels (FIG. 8). The protein expression was evaluated by using the commercial antibodies for OCT4, and NANOG. The results of the knockdown experiments indicated that infection of undifferentiated hESCs with ZNF206 shRNA-C lentivirus particles was the most potent down-regulator of ZNF206 mRNA and protein expression levels. In addition, we preliminarily observed that OCT-4 and NANOG expression were also indirectly down-regulated as a result of knocking down ZNF206 protein expression. SSEA-4, a surface marker on undifferentiated hESCs was also down-regulated. Since OCT-4 and NANOG expression are required to maintain hESCs undifferentiated and pluripotent, our results strongly suggested that ZNF206 expression is associated with (and perhaps essential) for hESC self-renewal and pluripotency.

Down-Regulation of ZNF206 Protein Expression Induces hESCs to Differentiate Along the Extra-Embryonic Endodermal Lineage. Since ZNF206 is differentially expressed between undifferentiated hESCs and primitive endoderm-like (PEL) cells (FIG. 2A), we decided to also determine if knocking down ZNF206 expression in undifferentiated hESCs causes them to differentiate along the extra-embryonic endoderm lineage. To determine this, we infected H9 hESCs with ZNF206 shRNA-C lentiviral expression particles. Consistent with our previous experiments, after four days, the hESC colonies that were infected with the ZNF206 shRNA-C lentiviral expression particles had a differentiated morphology. Analysis of the ZNF206 shRNA-C infected hESC colonies by immunofluorescence indicated that the knockdown of ZNF206 caused the majority of the hES cells to expressed SSEA-1, a specific surface marker of differentiated hESCs and, within the positive population of SSEA-1-expressing cells, were cells that co-expressed GATA6 (an early marker of the primitive endoderm lineage). Further analysis using RT-PCR indicated that down-regulating the expression of ZNF206 in hESCs causes them to up-regulate the expression of genes associated with the extra-embryonic endodermal lineage, e.g., GATA4, GATA6, SOX7, CouptfI and CouptfII.

The Role of ZN206 in hESCs and By Extension, Human Embryonic Development.

Figure 9A:
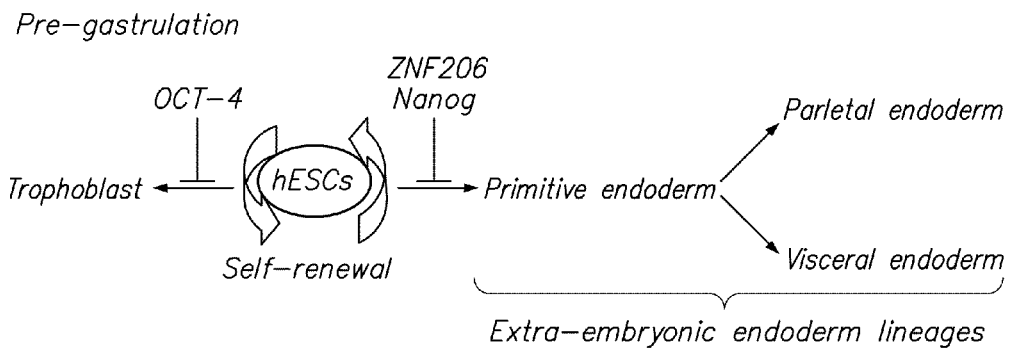
FIG. 9 shows the hypothesized Role of ZN206 in hESCs. [A] In our model, OCT4 is the key inhibitor of trophoblast differentiation in hESCs (since specific down-regulation of OCT-4 in hESCs leads to trophoblast differentiation), while NANOG and ZNF206 are key inhibitors of extra-embryonic endoderm lineage differentiation (since specific down-regulation of NANOG or ZNF206 leads to extra-embryonic endoderm lineage differentiation). For example, down-regulation of ZNF206 expression in hESCs causes them to upregulate genes associated with the extra-embryonic endoderm lineage (e.g., GATA4, GATA6, SOX17, AFP and HNF4A). [B] We further hypothesize that extra-embryonic endoderm differentiation may be the earliest default pathways for hESCs, particularly when dissociated into single cells and grown in defined, serum-free, feeder-free conditions. This default lineage may then help instruct the emergence of other lineages, e.g., neuroectoderm (perhaps giving the appearance of being default).
Figure 9B:
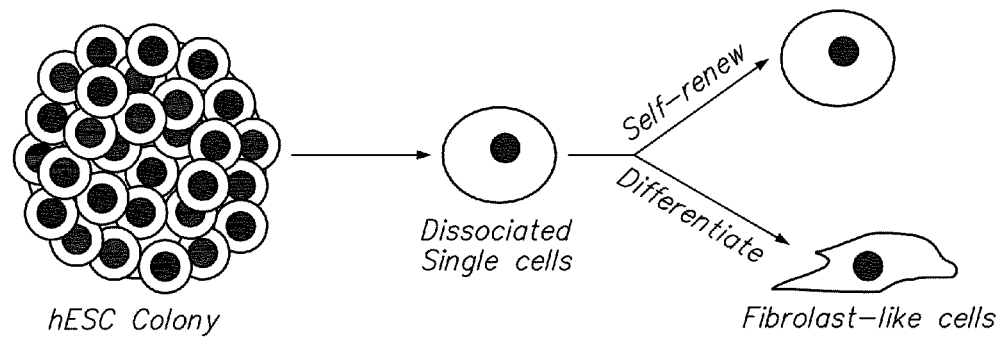

As indicated in the model depicted in FIG. 9, our studies show that extra-embryonic endoderm lineage appears to be the earliest default pathway for hESC differentiation (even prior to neuroectoderm—indeed, perhaps helping to instruct the formation of neuroectoderm), particularly when hESCs are dissociated into single cells and grown in defined, serum-free, feeder-free conditions. This default lineage may then help instruct the emergence of other lineages, e.g., neuroectoderm (perhaps giving the appearance of being default). In our model, OCT4 is the key inhibitor of trophoblast differentiation in hESCs (since specific down-regulation of OCT-4 in hESCs leads to trophoblast differentiation), while NANOG and ZNF206 are key inhibitors of extra-embryonic endoderm lineage differentiation (since specific down-regulation of NANOG or ZNF206 leads to extra-embryonic endoderm lineage differentiation). For example, down-regulation of ZNF206 expression in hESCs causes the upregulation of genes in the hESCs that are associated with the extra-embryonic endoderm lineage (e.g., GATA4, GATA6, SOX17, AFP and HNF4A). Repressing extra-embryonic endoderm development preserves the pluripotent state of hESCs (and perhaps, by extension, the ICM), and, conversely downregulating expression of ZNF206 in hESCs causes them to upregulate the expression of genes associated with the extra-embryonic endodermal lineage, down-regulate genes associated with the pluripotent state, and perhaps lead to the further emergence of genes associated with even more differentiated lineages and phenotypes.

FIG. 10 provides the nucleotide sequence of four isoforms of ZNF206.

EXAMPLE 2

As discussed in Example 1 above, the discovery of ZNF206 was one of the byproducts of having devised an entirely defined medium for growing human embryonic stem cells (hESCs). Briefly, we determined the minimal essential components of a defined culture system that could stably maintain hESCs in a self-renewing pluripotent state and serve as a platform for directing such hESCs towards particular differentiated cell types efficiently and exclusively using small molecules inducers, without an intervening multi-lineage embryoid body (EB) stage. In this culture system, hESCs spontaneously form an autogenic supportive niche composed of what proved to be primitive endoderm (PE) cells that could, in turn, support efficient clonal expansion and long-term self-renewal of hESCs, presumably providing paracrine support in vitro, much as the PE does for epiblast in vivo. High-throughput genomic and proteomic analysis of this clonally-related hESC-derived PE—when compared with the undifferentiated starting hESCs—allowed us to identify a novel Zinc finger protein (ZNF206) that was found to maintain hESC renewal and pluripotency by repressing PE lineage commitment.

Activin A is the Predominant Paracrine Factor Enabling hESC Growth

Our further analysis suggests that Activin A, which is secreted by hESC-derived primitive endoderm-like (PEL) cells (and the signal transduction pathway it activates) is the predominant paracrine factor enabling hESC clonal growth in a feeder-free minimal essential chemically-defined culture system.

Table 1 below provides a selective list of potential hESC growth-supporting proteins identified specifically in PEL- (but not human fibroblast [Hs27]-) conditioned medium (CM) by MudPit (Multidimensional Protein Identification Technology) proteomic analysis followed by Western blotting analysis. To meet the criteria, a peptide had to be detected three or more times (sequence count) and 10 percent or more of the protein sequence had to be detected (sequence coverage).

mediated activation of the Activin-A receptorIIA/B-Smad2/3 signaling pathway is required to maintain undifferentiated hESC growth. When specific inhibitors of Activin A (anti-Activin A, soluble ACVR2A/B-FC receptors, or SB-431542) were added to PE culture medium, the PE culture medium lost its ability to support clonal hESC expansion for both WA09 (H9) and WA01 (H1) cells. Hence, ZNF206 appears to regulate not only the emergence of extra-embryonic endoderm, but also the spontaneous secretion of members of the critical Activin pathway.

shRNA-Mediated Knock-Down of ZNF206 Causes hESCs to Lose Pluripotency

Using Western blots, we determined that short-hairpin (sh) RNA-mediated knock-down of ZNF206 causes hESCs to lose pluripotency and differentiate into extra-embryonic endoderm. ZNF206 knock-down alone was sufficient to abrogate Oct-4 and Nanog expression, suggesting it may work either upstream or in a critical complex with these known canonical "pluripotency genes", and likely establishing ZNF206 as an equally pivotal mediator of pluripotence—perhaps even essential for the proper expression and functioning of Oct-4 and Nanog.

RT-PCR was used to demonstrate the new expression of extra-embryonic lineage markers (GATA4, GATA6, SOX7, AFP and HNF4A) coincident with the loss of pluripotency marker expression (Oct-4, Nanog, Sox2); however, expression of trophoblastic markers (i.e., Cdx2, HCGα, HGGβ) was not turned on.

Immunofluorescence staining was used to illustrate the effect of ZNF206 on the actual expression of markers within H9 (WA09) hESC colonies infected with ZNF206 shRNA-C lentiviral expression particles. Immunofluorescence demonstrated the expression of the differentiation hESC surface marker SSEA-1 and the emergence of expression of the primitive endoderm (PE) early marker GATA-6 ectopically within the formerly undifferentiated colong (i.e., PE-like cells). These studies confirmed that knockdown of ZNF206 induces hESCs to differentiate alone the extra-embryonic endodermal lineage.

TABLE 1

Potential hESC growth supporting proteins

| Accession number | Protein name | Hs27-CM | | | PEL-CM | | |
|---|---|---|---|---|---|---|---|
| | | Seqcount | SpecCount | SeCov (%) | Seqcount | SpecCount | SeCov (%) |
| IPI00009720 | Leukemia inhibitory factor | x | x | x | 3 | 9 | 10 |
| IPI00008780 | Stanniocalcin-2 | x | x | x | 4 | 16 | 22 |
| IPI00028670 | Inhibin β A (Activin A) | x | x | x | 12 | 24 | 30 |
| IPI00007960 | Periostin | x | x | x | 57 | 244 | 46 |
| IPI00215630 | Versican | x | x | x | 6 | 15 | 10 |
| IPI00220156 | Transforming growth factor β2 | x | x | x | 3 | 5 | 11 |

SpecCount = number of times a peptide for the corresponding protein was identified.
x = Not detected Activin A added to our minimum essential defined culture medium (before spontaneous PE formation) can substitute in large measure for PE paracrine factors to maintain hESC pluripotency as assessed by the ability to promote hESC colony formation from a single cell. We found that the PE- Indeed, ZNF206-shRNA treated hESCs and PE cells have overlapping global gene expression profiles. Microarray gene expression was used to compare hESCs (line WA09 [H9]) treated with ZNF206 shRNA expression particles and human heart, brain, and liver tissues and hESC-derived primitive endoderm cells. The gene profiles of primitive endoderm and hESCs in which ZNF206 was suppressed were virtually identical. However there was very little overlap when such ZNF206-suppressed HSCs were compared with other cell types.

Overexpression of ZNF206 in PE Cells Induces Dedifferentiation into Pluripotent Cells Most intriguing, however, is the role that ZNF206 may play in a reprogramming process. As indicated above, we determined that ZNF206 could maintain hESC renewal and pluripotence by repressing constitutive PE lineage commitment. We also found that overexpression of ZNF206 alone in PE cells induced them to dedifferentiate—become "reprogrammed—back into pluripotent cells, as demonstrated in dedifferentiated PE cells that were immunostained for intracellular (Oct4, alkaline phosphatase) and surface markers of pluripotence (SSEA-4, Tra-1-80, Tra-1-60). Cells reprogrammed with the single factor ZNF206 not only looked like hESCs but also appeared to be identical to induced pluripotent somatic cells (IPSCs) generated from skin fibroblasts using the classical "four-factor cocktail" of Oct4, c-myc, Sox-2 and flf-4.

This result becomes intriguing in light of recent reports that their most efficient reprogramming occurs in "fibroblasts" generated from hESCs. We suspect these are not actually fibroblasts but rather PE, suggesting that ZNF206 may be a simpler biologically faithful method for dedifferentiation. In other words, under some circumstances, this single factor ZNF206 may be sufficient for generating induced pluripotent somatic cells (iPSCs), rather than the four factors usually required. The reprogrammed cells obtained by this method appear to be identical to those obtained using Oct4, c-myc, sox-2, & flf4 retrovirally transduced into skin cells.

All publications, patents and patent applications are incorporated herein by reference. While in the foregoing specification, this invention has been described in relation to certain embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An in vitro method of maintaining expression of pluripotency markers present in a cultured pluripotent cell comprising:
   (a) introducing into said cultured pluripotent cell a retroviral vector comprising a nucleic acid encoding a ZNF206 polynucleotide selected from the group consisting of SEQ ID NOS: 34-37 operably linked to a promoter; and
   (b) expressing the ZNF206 polypeptide encoded by the selected ZNF206 polynucleotide in said cultured pluripotent cell, wherein said expression of said ZNF206 polypeptide maintains expression of pluripotency markers in the cultured pluripotent cell.

2. An in vitro method of inducing expression of pluripotency markers present in a cultured differentiated cell comprising:
   (a) introducing into said cultured differentiated cell a retroviral vector comprising a nucleic acid encoding a ZNF206 polynucleotide selected from the group consisting of SEQ ID NOS: 34-37 operably linked to a promoter; and
   (b) expressing the ZNF206 polypeptide encoded by the selected ZNF206 polynucleotide in said cultured differentiated cell, wherein said expression of said ZNF206 polypeptide induces expression of pluripotency markers in the cultured differentiated cell.

3. The method of claim 1, wherein the cultured pluripotent cell is an embryonic stem cell.

4. The method of claim 3, wherein the cultured pluripotent cell is a human embryonic stem cell.

5. The method of claim 1, wherein the retroviral vector is a lentiviral vector.

6. The method of claim 1, wherein the pluripotency markers are selected from the group consisting of: Oct4, alkaline phosphatase, SSEA-4, Tra-1-80, and Tra-1-60.

7. The method of claim 2, wherein the retroviral vector is a lentiviral vector.

8. The method of claim 2, wherein the pluripotency markers are selected from the group consisting of: Oct4, alkaline phosphatase, SSEA-4, Tra-1-80, and Tra-1-60.

* * * * *